US012727855B2

(12) United States Patent
Shelton et al.

(10) Patent No.: US 12,727,855 B2
(45) Date of Patent: Sep. 8, 2026

(54) REPEATABLE ULTRASOUND

(71) Applicant: FUJIFILM SonoSite, Inc., Bothell, WA (US)

(72) Inventors: Daniel Shelton, Prosper, TX (US); Christopher Howard, Seattle, WA (US)

(73) Assignee: FUJIFILM SonoSite, Inc., Bothell, WA (US)

(*) Notice: Subject to any disclaimer, the term of this patent is extended or adjusted under 35 U.S.C. 154(b) by 219 days.

(21) Appl. No.: 18/436,699

(22) Filed: Feb. 8, 2024

(65) Prior Publication Data

US 2025/0255579 A1 Aug. 14, 2025

(51) Int. Cl.
*A61B 8/00* (2006.01)

(52) U.S. Cl.
CPC .............. *A61B 8/4218* (2013.01); *A61B 8/40* (2013.01); *A61B 8/4281* (2013.01); *A61B 8/54* (2013.01)

(58) Field of Classification Search
CPC ....... A61B 8/4218; A61B 8/40; A61B 8/4281; A61B 8/54
See application file for complete search history.

(56) References Cited

U.S. PATENT DOCUMENTS 6,425,865 B1 * 7/2002 Salcudean ............. A61B 34/32 600/437
2008/0210009 A1 * 9/2008 Tanishiki ............. G01N 29/043 73/588
2011/0125022 A1 5/2011 Lazebnik
2014/0163377 A1 * 6/2014 Kang .................. A61B 8/0875 600/447
2017/0252002 A1 * 9/2017 Mine .................... A61B 8/4218
2020/0323540 A1 * 10/2020 Kang ..................... A61B 17/14
2020/0346046 A1 * 11/2020 Cannata .................. A61N 7/00
2020/0405417 A1 * 12/2020 Shelton, IV ......... A61B 90/361
2021/0282858 A1 * 9/2021 Hill ........................ A61B 34/76
2022/0031395 A1 * 2/2022 Bono ..................... A61B 34/20
2022/0218422 A1 * 7/2022 Khurana ................ A61B 34/32
(Continued)

FOREIGN PATENT DOCUMENTS

WO 2023067587 A1 4/2023

OTHER PUBLICATIONS

"Non-Final Office Action", U.S. Appl. No. 18/975,909, Mar. 20, 2026, 43 pages.

*Primary Examiner* — Dixomara Vargas
(74) *Attorney, Agent, or Firm* — Colby Nipper PLLC

(57) ABSTRACT

Systems and methods for repeatable ultrasound are disclosed. These systems and methods enable generation of consistent ultrasound images across serial ultrasound examinations, which are suitable for the early detection and management of one or more medical conditions, including rheumatoid arthritis. These systems can include a robotic manipulator that holds and operates an ultrasound scanner for scanning a patient's anatomy. Additionally, sensors are used to detect position and orientation of the patient anatomy to enable the robotic manipulator to consistently hold and orient the ultrasound scanner based on the position and orientation of the patient anatomy during an ultrasound examination. In aspects, an anatomy fixture can be generated to support the patient anatomy in the same position and orientation across the serial ultrasound examinations.

20 Claims, 14 Drawing Sheets

(56) References Cited

U.S. PATENT DOCUMENTS

| | | | | |
|---|---|---|---|---|
| 2023/0038498 | A1* | 2/2023 | Xu | A61B 34/30 |
| 2023/0061534 | A1* | 3/2023 | Stopek | A61B 34/25 |
| 2023/0218930 | A1* | 7/2023 | Stopek | A61B 8/085 601/3 |
| 2023/0255701 | A1* | 8/2023 | Post | A61B 34/30 606/82 |
| 2024/0139552 | A1* | 5/2024 | Duryea | A61B 34/10 |
| 2024/0139553 | A1* | 5/2024 | Miller | B06B 1/0215 |
| 2024/0189627 | A1* | 6/2024 | Bogott | A61N 7/00 |
| 2024/0285355 | A1* | 8/2024 | Sudre | A61B 34/30 |
| 2024/0341891 | A1 | 10/2024 | Helm et al. | |
| 2024/0350153 | A1* | 10/2024 | Cannata | A61B 8/4218 |
| 2025/0009445 | A1* | 1/2025 | Balicki | A61B 8/4245 |
| 2025/0090871 | A1* | 3/2025 | Snell | G16H 20/40 |
| 2025/0160787 | A1* | 5/2025 | Krieger | A61B 8/4245 |
| 2026/0157725 | A1 | 6/2026 | Zhang et al. | |

* cited by examiner

100
Scanner Holder
114
Scanner(s)
116
Scanner
Robotic Manipulator
112
Scanner
116-1
134
138
Scan Data
Scan Instructions
142
Movement Instructions
136
Scanner-
Configuration Data
140
Processor System
110
Position Controller
108
Images
132
Database
130
Registration Data
128
Image-Based 128-1
Sensor-Based 128-2
Anatomy-Registration Data
126
Fixture Generator
104
Anatomy-Capture
Device
106
Anatomy Fixture
124
Patient Anatomy
120
118
122
102
120-1

400

500

600

700

800

900

1100

REPEATABLE ULTRASOUND

BACKGROUND

Ultrasound systems can generate ultrasound images by transmitting sound waves at frequencies above the audible spectrum into a body, receiving echo signals caused by the sound waves reflecting from internal body parts, and converting the echo signals into electrical signals for image generation. Because they are non-invasive and non-ionizing, ultrasound systems are used ubiquitously. One example where ultrasound systems are used is rheumatology.

Rheumatology treats auto-immune disorders that attack a patient's joint lining, including rheumatoid arthritis that is common in hands and feet. If not detected early, rheumatoid arthritis can erode and permanently damage the patient's joint, and even progress to the bone. Some imaging techniques other than ultrasound can be used, such as X-ray and magnetic resonance imaging (MRI); however, X-ray is poor at detecting erosion caused by rheumatoid arthritis and therefore poor at early detection, and MRI is often not accessible, or is too expensive, for many patients. Hence, detection and monitoring of rheumatoid arthritis via ultrasound is common.

Treatment of rheumatoid arthritis usually includes serial ultrasound scanning over multiple examinations that occur periodically, e.g., every three months. For proper assessment of the progression of rheumatoid arthritis, it is imperative that the images generated during these multiple examinations have essentially identical views. However, operator dependency (among different examinations and/or different operators) can prevent the level of reproducibility needed to generate matching image views. Moreover, the weight of a gel pad used in some ultrasound examinations is often large enough to cause compression of the synovium or swollen joint lining, skewing imaging results.

Hence, many ultrasound operators often use a coupling gel instead of a gel pad. However, floating the ultrasound scanner in the gel at a constant height above the patient and without touching the patient requires extensive training and experience, and is simply not achievable for most ultrasound operators. This deficiency can prevent the generation of matching image views needed in the serial ultrasound examinations.

In some cases, a water bath is used in lieu of gel pads and coupling gel. However, the ultrasound operator is required to consistently float the scanner in the water relative to the patient anatomy. Similar to the use of coupling gel, this is simply not achievable for most ultrasound operators who usually tilt the scanner, resulting in inconsistent and unusable imaging results. Further, the motion of the water in the water bath (e.g., introduced by the movement of the scanner, such as when an operator does not smoothly move the scanner) can introduce noise artifacts for some imaging modes, such as color Doppler. Moreover, many ultrasound scanners are simply not approved for submersion in water.

Accordingly, conventional ultrasound systems may not be suitable for the assessment of certain medical conditions, such as rheumatoid arthritis, and the use of these conventional ultrasound systems can result in poor patient care, including permanent joint damage. In some examples, the poor patient care includes prolonged use of chemotherapy drugs during treatment that could be reduced or eliminated if the medical condition (e.g., rheumatoid arthritis) were detected and treated early.

SUMMARY

Systems and methods for repeatable ultrasound are disclosed. These systems and methods enable generation of consistent ultrasound images across serial ultrasound examinations, which are suitable for the early detection and management of certain medical conditions, including rheumatoid arthritis. These systems can include a robotic manipulator that holds and operates an ultrasound scanner for scanning a patient anatomy. Additionally, sensors can be used to detect position and orientation of the patient anatomy to enable the robotic manipulator to consistently hold and orient the ultrasound scanner based on the position and orientation of the patient anatomy during an ultrasound examination. In aspects, an anatomy fixture can be generated to support the patient anatomy in the same position and orientation across the serial ultrasound examinations.

In some aspects, an ultrasound system is disclosed. The ultrasound system includes an ultrasound scanner, a robotic manipulator, a processor system, an adaptive-registration system, and a database. The ultrasound scanner is configured to generate ultrasound data based on received reflections of ultrasound signals transmitted by the ultrasound scanner at a patient anatomy. The robotic manipulator is configured to couple to the ultrasound scanner, the robotic manipulator configured to control positioning, movement, and operation of the ultrasound scanner. The processor system is configured to generate scan instructions for the robotic manipulator and receive the ultrasound data from the ultrasound scanner. The adaptive-registration system is configured to determine a position and orientation of the patient anatomy and adjust the robotic manipulator to orient the ultrasound scanner based on the determined position and orientation of the patient anatomy. The database is configured to store data corresponding to the ultrasound data and anatomy-registration data associated with the determined position and orientation of the patient anatomy.

In some aspects, a method for repeatable ultrasound is disclosed. The method includes providing a vessel having an interior volume, detecting exterior boundaries of a patient anatomy located within the interior volume of the vessel, and detecting a spatial relation of the patient anatomy relative to the vessel. The method also includes generating anatomy-registration data corresponding to the patient anatomy based on the spatial relation of the patient anatomy relative to the vessel and the exterior boundaries of the patient anatomy. Further, the method includes determining movement instructions for a robotic manipulator based on the anatomy-registration data and providing the movement instructions to the robotic manipulator to move and operate an ultrasound scanner for scanning the patient anatomy.

BRIEF DESCRIPTION OF THE DRAWINGS

The appended drawings illustrate examples and are, therefore, exemplary embodiments and not considered to be limiting in scope. Throughout the drawings, the same numbers are used to reference like features and components.

DETAILED DESCRIPTION

Figure 1:
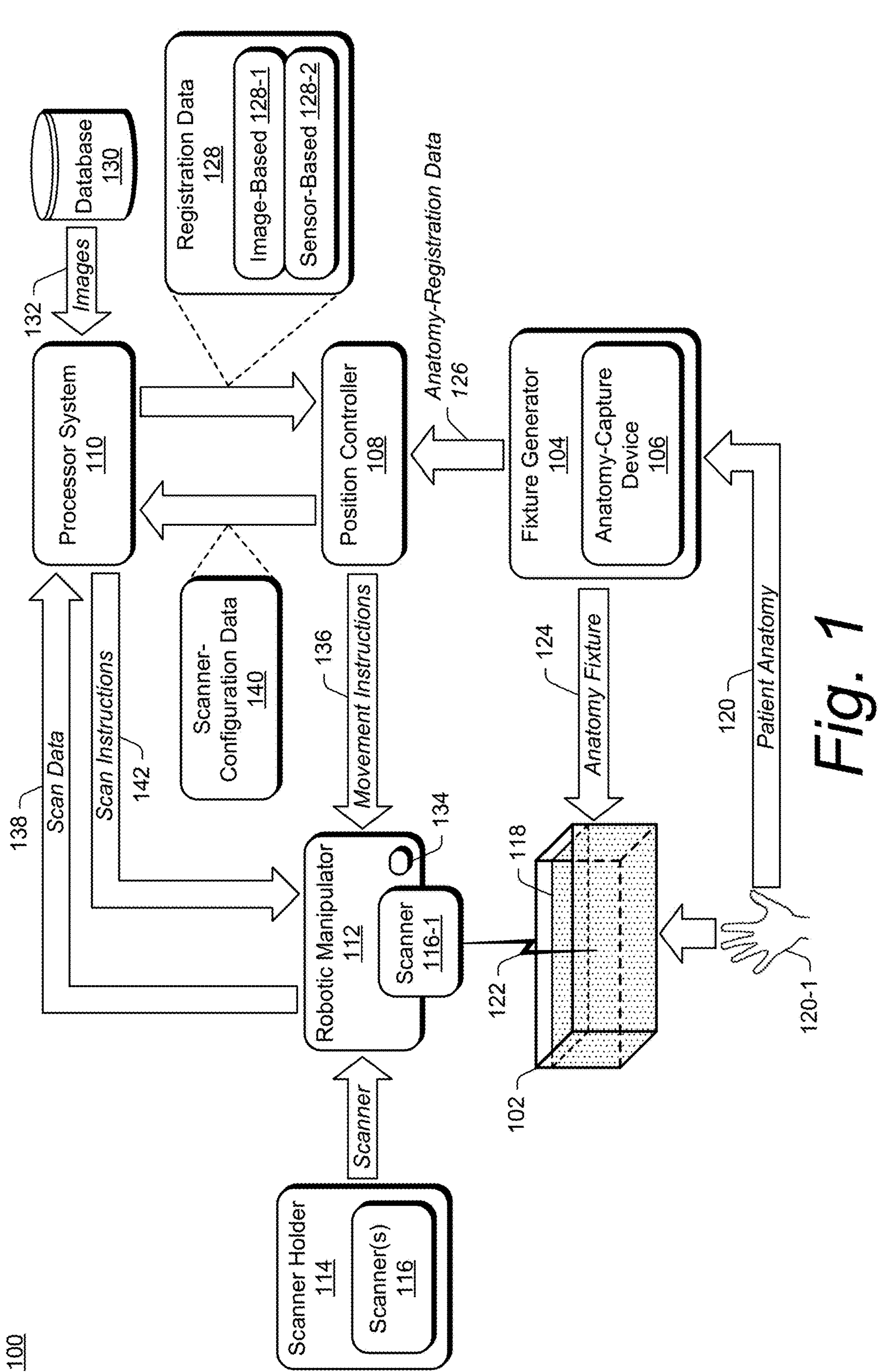
FIG. 1 illustrates an ultrasound system for generating consistent ultrasound images suitable for the early detection and management of one or more medical conditions.

Disclosed herein are systems and methods for repeatable ultrasound. Conventional ultrasound systems may not be suitable for the assessment of some medical conditions, such as rheumatoid arthritis, and the use of such conventional ultrasound systems can result in poor patient care, leading to permanent joint damage. In some examples, the poor patient care includes the prolonged use of chemotherapy drugs during treatment that could be reduced or eliminated if the rheumatoid arthritis could be detected and treated early.

Accordingly, systems, devices, and techniques are disclosed herein for generating consistent ultrasound images suitable for the early detection and management of one or more medical conditions. An ultrasound system in accordance with the present invention includes a vessel that can contain a coupling agent, such as water or gel. The ultrasound system includes a robotic manipulator, which is a reprogrammable and multifunctional mechanical device capable of moving objects or tools through programmed motions to perform various tasks. The robotic manipulator can be, for example, a robotic arm or multi-axis mill, which can hold and consistently orient an ultrasound scanner or can include one or more dedicated and/or integrated acoustic ultrasound arrays. The ultrasound system includes an ultrasound scanner holder that can hold multiple ultrasound scanners, each of which can be retrieved by the robotic manipulator.

The ultrasound system also includes a registration system, such as an adaptive-registration system, which determines a position and orientation of a patient anatomy before, during, and after an ultrasound examination and adjusts the robotic manipulator to orient the scanner based on the position and orientation of the patient anatomy during the ultrasound examination. In embodiments, the adaptive-registration system includes electronic sensors to determine the position and orientation of the patient anatomy. Additionally or alternatively, the adaptive-registration system can include a mechanical anatomy fixture used to determine the position and orientation of the patient anatomy. Hence, the ultrasound system reduces and/or removes the dependency of the operator and inconsistencies resulting from patient movement, so that the ultrasound system can generate matching image views needed in serial ultrasound examinations for the assessment and treatment of a medical condition such as rheumatoid arthritis.

Using the techniques described herein facilitates remote and in-person examinations, supports both procedural and diagnostic purposes, and enables the use of interchangeable scanners that can consistently and repeatedly follow the same path and generate matching image views even when different scanners or transducers are used. Also, these techniques can be operator independent and can be implemented via a mobile ultrasound system or a fixed ultrasound system. Accordingly, the disclosed techniques enhance the user experience and can provide more accurate ultrasound data for serial examinations, in comparison to conventional ultrasound systems.

Example Ultrasound System

FIG. 1 illustrates an ultrasound system 100 for generating consistent ultrasound images suitable for the early detection and management of one or more medical conditions. The ultrasound system 100 includes a vessel 102, a fixture generator 104 that can include an anatomy-capture device 106, a position controller 108, a processor system 110, a robotic manipulator 112, and a scanner holder 114 that can hold multiple ultrasound scanners 116, also referred to as ultrasound probes and/or ultrasound transducers. In some aspects, the scanner holder 114 can hold multiple transducer arrays or scan heads that are interchangeable with a single scanner body.

The vessel 102 can include any suitable container that can hold a coupling agent 118, such as water or gel, which conforms to a patient anatomy 120 (e.g., hand 120-1) and enables the patient anatomy 120 to be inserted into the vessel 102 for scanning via a selected ultrasound scanner 116-1. Although the examples described herein relate to a human such as a human hand, the patient anatomy 120 can be any tissue or anatomy that can be penetrated by ultrasound, including that of animals, plants, insects, etc. The scanning includes transmitting and receiving ultrasound signals 122. The coupling agent 118 acts as a conductor that facilitates the transmission of the ultrasound signals 122 between the ultrasound scanner 116 and the patient anatomy 120. In aspects, the coupling agent 118 includes a medication, such as a pain medication. For instance, the patient anatomy 120 can be injured and have foreign objects embedded in their anatomy, such as glass shards or plastic shrapnel. In an example, the coupling agent 118 includes a gas, such as a dense or foggy gas for coupling the ultrasound scanner 116-1 to the patient anatomy 120 to provide a medium for conducting the ultrasound signals 122. In some aspects, the ultrasound system 100 applies the coupling agent 118 during the examination, such as with a nozzle attached to the robotic manipulator 112. The nozzle can dispense the coupling agent 118 to the patient's skin as the scanner 116-1 is moved along the patient to image the patient anatomy 120.

The robotic manipulator 112 can be implemented to hold and control one or more interventional instruments to enable the ultrasound system 100 to be used for both diagnostic and procedural purposes. The robotic manipulator 112 is a robotic mechanism or device, such as an automated machine, which has joints and rigid links and is programmable to move in multiple degrees of freedom (e.g., six degrees of freedom). In an example, a user can select a point of an ultrasound image displayed on a display of the ultrasound system 100 and the ultrasound system 100 automatically inserts an interventional instrument (e.g., needle) to guide the tip to the user-selected point. Moreover, the ultrasound system 100 can be operated by a remote user, supporting remote assessment and procedures as well as telemedicine. In some embodiments, the ultrasound system 100 is portable. A portable ultrasound system can, for example, be configured in a way that it fits in a hand-carried bag, and/or can be assembled and placed on a desk-top, table, or medical cart. In other embodiments, the ultrasound system is fixed (e.g., stationary system in a care facility, such as a rack-mounted ultrasound system).

Examples of the patient anatomy 120 are not limited to hands and/or feet and can include any anatomy that generally is scanned using a stringent protocol that requires repeatable imaging. Hence, the patient anatomy 120 can include elbows, knees, wrists, ankles, shoulders, etc. For instance, assessment and treatment of a rotator-cuff injury requires consistent scans across multiple ultrasound examinations, similar to that needed for the assessment and treatment of rheumatoid arthritis. Further, the patient anatomy 120 can include areas of the body that have synovial tissue, such as tendons, joint capsules, and joint membranes. The patient anatomy 120 can also include other types of tissue than synovial tissue, such as muscles. For instance, detection and treatment of atrophy requires multiple studies repeated every few months, and consistent imaging results. The patient anatomy 120 can also include skin, for the tracking of skin lesions, such as skin cancers, which can require repeatable scans over multiple examinations. Accordingly, the techniques disclosed herein are not limited to detecting and managing rheumatoid arthritis; this disease is described throughout the specification for exemplary purposes and is not meant to be limiting.

To accommodate these various patient anatomies, the vessel 102 can be of any suitable shape and size. In an example, the vessel 102 includes a bucket or open container. In another example, the vessel 102 includes a bladder. The bladder can be of sufficient size so that the patient anatomy 120 fits inside the vessel 102. In an example, the vessel 102 includes a tank in which the patient can fit inside (e.g., by laying down, sitting, or standing). In aspects, the vessel 102 includes a port on a portion of the vessel 102 (not shown in FIG. 1 for clarity), such as on the side of the vessel 102. The port can facilitate insertion of the patient anatomy 120 into the vessel 102 and prevent the coupling agent from leaking out of the vessel 102.

The fixture generator 104 receives the patient anatomy 120 (illustrated in FIG. 1 as hand 120-1) and generates an anatomy fixture 124 from the patient anatomy 120. The anatomy fixture 124 can subsequently support the patient anatomy 120 in the vessel 102 during an ultrasound examination. In aspects, the fixture generator 104 includes an anatomy-capture device 106 that captures (e.g., senses, detects, measures, etc.) various characteristics of the patient anatomy 120, such as shape, size, orientation, etc., in a three-dimensional coordinate system (or a four-dimensional (4D) coordinate system including a time element). The fixture generator 104 can then generate the anatomy fixture 124 from the characteristics of the patient anatomy 120 determined by the anatomy-capture device 106. In an example, the anatomy-capture device 106 generates the negative, or inverse, of the patient anatomy 120 as the shape. For instance, the anatomy-capture device 106 can generate a mold of the patient anatomy 120, where the mold includes an imprint (e.g., an impression defining a negative copy of the patient anatomy 120) usable to reproduce an outline of the patient anatomy 120. The mold can be created in any suitable way, some examples of which are described in detail below. In some cases, the anatomy-capture device 106 generates a three-dimensional (3D) computer model of the patient anatomy 120 based on sensor data from sensors (e.g., optical sensors, infrared sensors, LIDAR sensors, RF sensors, etc.) used to sense the characteristics and features of the patient anatomy 120. Then, the fixture generator 104 can generate a physical mold from the 3D computer model. Additionally or alternatively, the fixture generator 104 can generate the anatomy fixture 124 from the 3D computer model.

The anatomy fixture 124 can include the mold. The mold can subsequently receive the patient anatomy into the impression to cause the patient anatomy to be positioned in substantially the same orientation that it had when the anatomy-capture device 106 captured the characteristics of the patient anatomy 120 and created the mold. In some aspects, the fixture generator 104 includes a 3D printer that can 3D-print the anatomy fixture 124. In other aspects, at least a portion of the coupling agent 118 can be solidified, using the robotic manipulator 112 or an external energy source, to form the mold around the patient anatomy 120 for subsequent removal.

Alternatively or additionally, the fixture generator 104 can include a shape-adapting material (e.g., metamaterial, memory-shaping material) or mechanism that can be shaped and reshaped to generate the anatomy fixture 124. The anatomy fixture 124 and/or the vessel 102 can be part of an adaptive-registration system that generates position and orientation data of the patient anatomy 120 during an ultrasound examination, as illustrated in more detail in FIGS. 2 and 3.

Figure 2:
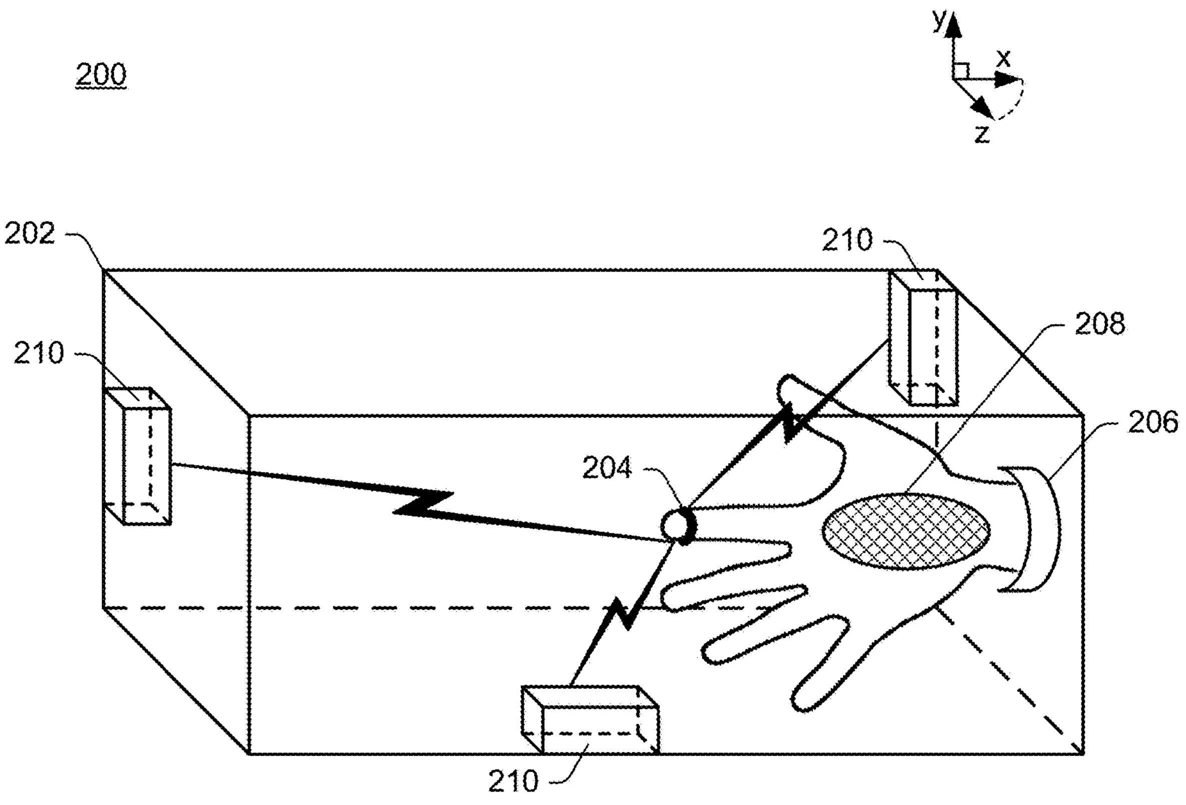
FIG. 2 illustrates an adaptive-registration system for generating consistent ultrasound images suitable for the early detection and management of one or more medical conditions.

FIG. 2 illustrates an adaptive-registration system 200 for generating consistent ultrasound images suitable for the early detection and management of one or more medical conditions. The adaptive-registration system 200 includes a vessel 202, which is an example of the vessel 102 in FIG. 1. The adaptive-registration system 200 also includes one or more patient-worn components (e.g., patient-worn components 204, 206, and 208), which can include sensors and/or actuators that are in communication with actuators and/or sensors 210 coupled or affixed to the vessel 202. The communication between the patient-worn components 204, 206, and 208 and the actuators and/or sensors 210 can include a wireless communication link, such as a near-field communication (NFC) link. For clarity, the communication is illustrated in FIG. 2 only for the patient-worn component 204; however, the communication can be with any combination of the patient-worn components 204, 206, and 208 and the actuators and/or sensors 210. As the patient moves the patient anatomy 120 inside the vessel 202 during an ultrasound examination, the ultrasound system 100 can determine anatomy-registration data that denotes a spatial relation (e.g., position and orientation) of the patient anatomy 120 with respect to the vessel 202 based on the respective positions of the patient-worn components 204, 206, and 208 as detected by the actuators and/or sensors 210. Any suitable positioning algorithm can be used, including triangulation in a Cartesian coordinate system, for example, to determine the spatial relation of the patient-worn components 204, 206, and 208 relative to the actuators and/or sensors 210. The patient-worn component 204 is illustrated as a ring. The patient-worn component 206 is illustrated as a wrist band. The patient-worn component 208 is illustrated as a patch affixed to the palm of the patient's hand or to a glove worn by the patient's hand. The patient-worn components 204, 206, and 208 are exemplary and not meant to be limiting. Further, the system can include any suitable number of patient-worn components.

Figure 3:
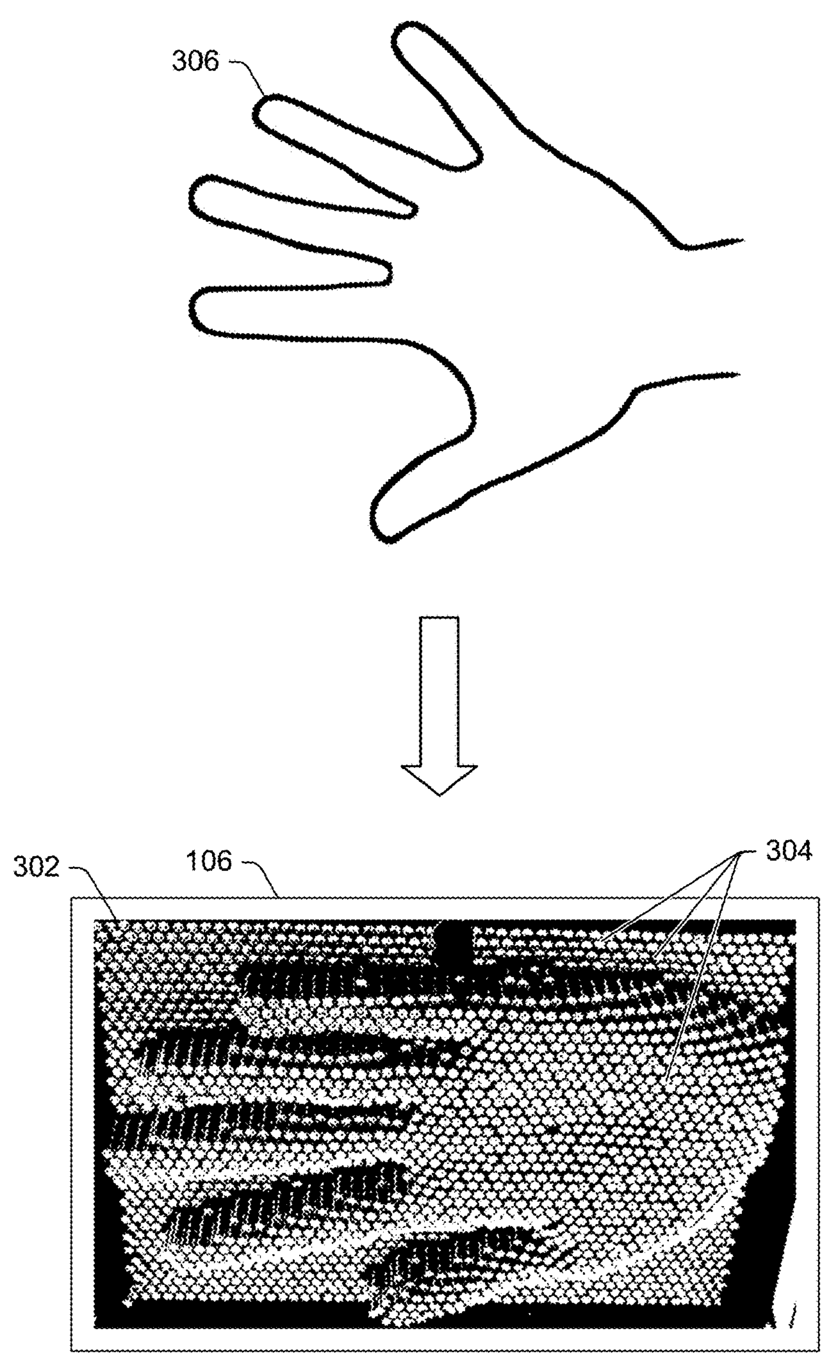
FIG. 3 illustrates an example implementation of an anatomy-capture device as part of the fixture generator from FIG. 1.

FIG. 3 illustrates an example implementation 300 of an anatomy-capture device 302 as part of the fixture generator 104 from FIG. 1. The anatomy-capture device 302 can be an implementation of or a component of the anatomy-capture device 106. The anatomy-capture device 302 includes an array of pins 304 that form an impression of a patient anatomy 306 (e.g., patient anatomy 120) when the patient anatomy 306 is pressed against the anatomy-capture device 302. The pins 304 each have a central axis and are each displaceable along their central axis. The pins 304 of the anatomy-capture device 302 can be spring loaded, so that when the patient anatomy 306 is removed from the anatomy-capture device 302, the pins 304 return to their default, upright position. The ultrasound system 100 can use sensors (e.g., a sensor on each pin 304) to detect the depth and location of each of the pins 304 as anatomy-registration data that represents the contour of the exterior surface of a portion of the patient anatomy 306 that contacted the pins 304, such as a lower half of the patient anatomy 306. The anatomy-registration data provides a position and orientation of the patient anatomy 306 with respect to the anatomy-capture device 302 and/or the vessel 202. For instance, the anatomy-capture device 302 can be anchored to the vessel 202 at a known position and orientation to define a fixed spatial relation between the anatomy-capture device 302 and the vessel 202.

In an example, settings (e.g., depth, location, etc.) of the array of pins 304 is recorded and used as an initialization setting for a subsequent examination. For instance, the array of pins 304 can be set during a subsequent examination based on the registration data determined during a current examination. Further, the settings can be used to establish boundaries of the patient anatomy 306 (e.g., location of exterior surfaces of the patient anatomy 306, size of hand, etc.), to prevent the ultrasound system from causing the ultrasound scanner to collide with the patient anatomy 306. In embodiments, the ultrasound system uses the array of pins 304 as a temporary fixture to generate the anatomy fixture 124 (shown in FIG. 1). For instance, the ultrasound system can include a 3D printer that prints the anatomy fixture 124 based on the settings of the array of pins 304. Additionally or alternatively, the ultrasound system can generate a prosthetic for the patient, or a cast (e.g., if the patient has an injury), with the 3D printer based on the settings of the array of pins 304.

In some implementations, the fixture generator 104 can use the anatomy-capture device 302 as the anatomy fixture 124 for subsequent ultrasound examinations. For example, the anatomy-capture device 302 can include one or more actuators (e.g., linear actuators, electromagnets, etc.) that can displace the pins 304 to move the pins 304 to their respective depth according to the initialization setting. The one or more actuators can displace at least a subset of the pins in the array of pins. Each pin 304 can be manipulated by a different actuator. Alternatively, a single actuator can move and position multiple pins 304. In an example, on a subsequent examination, the actuators can position the pins 304 to match the recorded settings of the array of pins 304. Then, the patient can place their anatomy into the impression created by the array of pins 304, which matches the position and orientation of the patient anatomy 306 from their previous examination (e.g., initial examination). In this way, the anatomy-capture device 302 becomes or acts as the anatomy fixture 124. Such an implementation can reduce the amount of materials and time needed to produce (e.g., 3D print) the anatomy fixture 124 because the actuators and the pins 304 enable the anatomy-capture device 302 to precisely recreate the same impression for the patient anatomy 306 each examination without additional materials. Such actuators and pins also enable the anatomy-capture device 302, acting as the anatomy fixture 124, to be dynamically adaptable to different patients.

Returning to FIG. 1, the fixture generator 104 provides anatomy-registration data 126 to the position controller 108. The anatomy-registration data 126 can include data generated by electrical and/or mechanical means, as described above with respect to FIGS. 2 and 3. The position controller 108 can also receive registration data 128 from the processor system 110. This registration data 128 can be image-based registration data 128-1 (e.g., determined based on ultrasound-image data generated by the ultrasound system 100). For instance, the processor system 110 can implement a machine-learned model that receives image data generated as part of a current ultrasound examination, as well as image data from a database 130 that maintains images 132 and/or ultrasound data (e.g., relative position and orientation of a patient anatomy) from previous ultrasound examinations. The machine-learned model can generate the image-based registration data 128-1 by processing the current and previous ultrasound-image data. The image-based registration data 128-1 can include dimensions in a coordinate system and/or angular dimensions that define movements for the robotic manipulator 112 and/or the scanner 116 to enable a current ultrasound image to have a matching view to a previous ultrasound image.

Additionally or alternatively, the registration data 128 from the processor system 110 can include sensor-based registration data 128-2. For example, the ultrasound system 100 can include a source and/or sensor 134 configured to scan the patient anatomy 120 while the patient anatomy is located in the vessel 102 to determine the position and/or orientation of the patient anatomy 120. The source and/or sensor 134 can be attached to the robotic manipulator 112, to enable movements of the source and/or sensor 134 to be fixed relative to the selected scanner 116-1. The source and/or sensor 134 can be based on light (e.g., a laser, light detection and ranging (LIDAR), etc.), radar, sonar, optical, non-visible spectrum electromagnetic (EM) radiation, and the like. In an example, the source and/or sensor 134 is implemented in the selected scanner 116-1 and uses ultrasound to generate the sensor-based registration data 128-2. In embodiments, the source and/or sensor 134 can include a line scanner. In embodiments, registration includes affixing a fiducial marker to the patient's skin, which can be detected via the source and/or sensor 134, such as a line scanner. A fiducial marker can include a coating, a grid, a tattoo, one or more marker dots, etc.

Additionally or alternatively to the source and/or sensor 134, the ultrasound system 100 can generate a scout image (e.g., a superficial or preliminary scan) to determine boundaries of the patient anatomy 120, which reduces the risk of causing the scanner 116-1 to collide with the patient anatomy 120. Further, the scout image can also be useful because the desired anatomy does not always follow the profile of the patient's skin, like an internal bone. Hence, it may be desirable to position and move the scanner 116 to follow the internal bone, not the skin, for proper imaging, while still avoiding a collision between the scanner 116 and the patient's skin.

In an example, the ultrasound system 100 generates an interventional instrument based on the registration data 128 and/or the ultrasound-image data to precisely fit the patient anatomy 120. For example, the ultrasound system 100 can use the registration data 128 and/or the ultrasound-image data to generate (e.g., 3D print) a curved needle that uniquely fits the patient anatomy 120 for a specific procedure. The needle can be printed with markers that are detectable via ultrasound, to help guide insertion of the needle during a procedure. Because the needle can be specifically generated based on the registration data so that it can be inserted in a specific way/trajectory to a specific patient anatomy, the markers printed on the needle can be placed at locations that the system determines are most likely to be detected via the ultrasound. The system can omit to print markers on locations of the needle that the system determines are not likely to be detected by the ultrasound. Hence, the system can generate the needle for a specific application for a specific patient, during an examination, rather than use a conventional needle, thus providing better needle-insertion guidance compared to use of a conventional needle.

The position controller 108 generates movement instructions 136 based on the registration data 128 from the processor system 110 and/or the anatomy-registration data 126 from the fixture generator 104 and/or the adaptive-registration system 200. The movement instructions 136 direct movement and operation of the robotic manipulator 112 to enable the selected scanner 116-1 to generate scan data 138 (e.g., ultrasound data) so that a current ultrasound image has a matching view to a previous ultrasound image (e.g., from a previous ultrasound examination). In aspects, the position controller 108 can use the registration data 128 and/or the anatomy-registration data 126 to determine boundaries of the patient anatomy 120 and generate the movement instructions 136 to prevent the robotic manipulator 112 from forcing the scanner 116 to collide with the patient anatomy 120.

The position controller 108 can also provide scanner-configuration data 140 to the processor system 110. The scanner-configuration data 140 can indicate position data for the scanner 116-1. For example, at various positions according to the scanner-configuration data 140, the scanner 116-1 can be enabled to transmit and receive ultrasound in a first configuration, and at various positions according to the scanner-configuration data 140, the scanner 116-1 can be enabled to transmit and receive ultrasound in a second configuration. The configurations can include any suitable data, such as a frequency, bandwidth, imaging mode, array selection, etc., for configuring the scanner 116-1. The processor system 110 receives the scanner-configuration data 140 from the position controller 108 and provides scan instructions 142 to the scanner 116-1. The processor system 110 also receives the scan data 138 (e.g., ultrasound imaging data) from the scanner 116.

The robotic manipulator 112 retrieves the scanner 116-1 from the scanner holder 114 and holds the scanner 116-1. The robotic manipulator 112 can hold the scanner 116-1 in numerous ways, some examples of which include using a biasing force to grip the scanner 116-1, a magnetic coupling, a threaded coupling, a snap-fit coupling, etc. In aspects, the robotic manipulator 112 is communicably coupled to the ultrasound scanner 116-1 such that the robotic manipulator 112 can pass instructions to the scanner 116-1 from the processor system 110. In some implementations, the robotic manipulator 112 provides power to the scanner 116-1, eliminating the need for the scanner 116-1 to use a battery or an independent power source. Providing power in this way can significantly reduce the heat generated by the scanner 116-1, providing better patient comfort and longer scan times with shorter dead times between scanning, compared to conventional ultrasound systems. The scan instructions 142 from the processor system 110 can be transferred through the robotic manipulator 112 to the scanner 116-1. Hence, the connection between the robotic manipulator 112 and the scanner 116-1 can include not only power but also data. Such a connection can also transfer the scan data 138 generated by the scanner 116-1 to the processor system 110. The scanner holder 114 can include any suitable device for holding, storing, and orienting the one or more scanners 116, as described in further detail in FIGS. 4-6.

Figure 4:
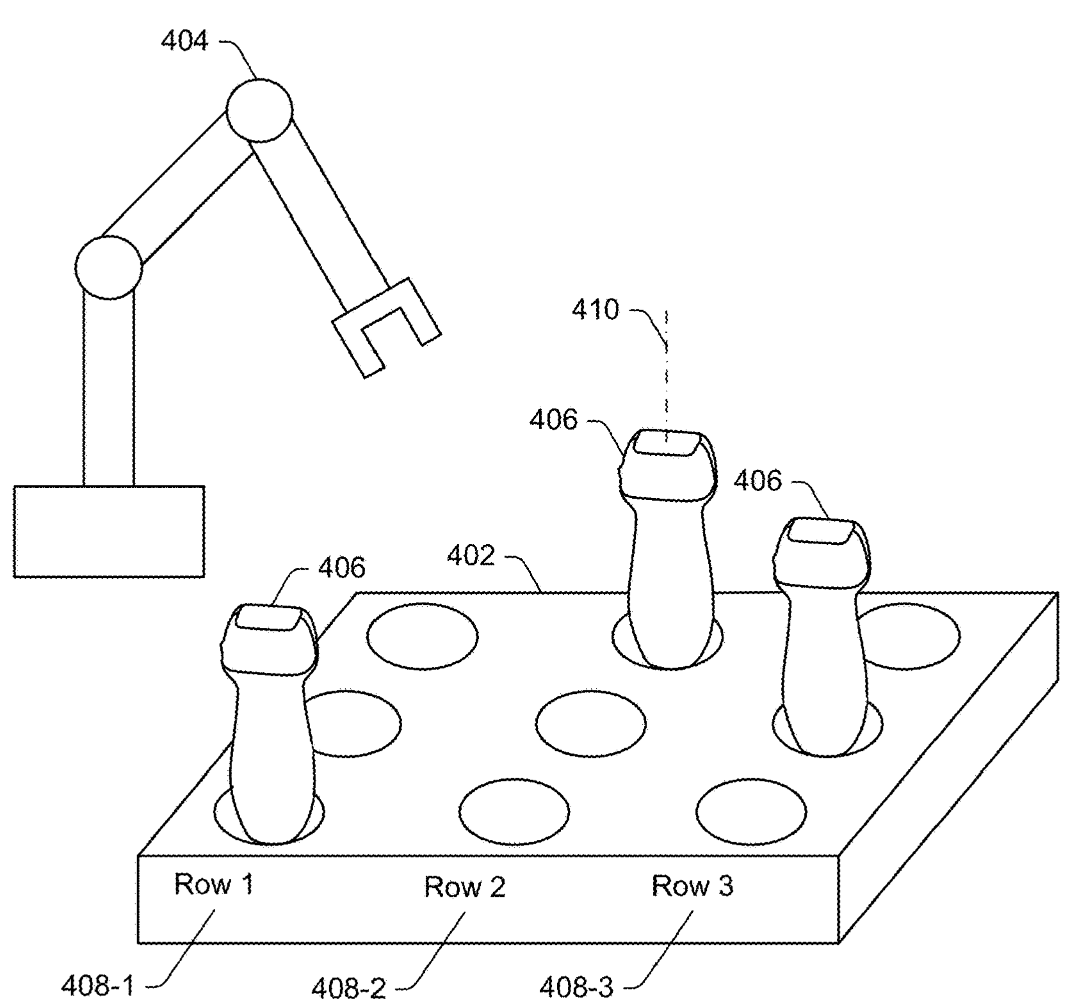
FIG. 4 illustrates an implementation of an example scanner holder, which is part of the ultrasound system from FIG. 1.

FIG. 4 illustrates an implementation 400 of an example scanner holder 402, which is part of the ultrasound system from FIG. 1. The scanner holder 402 is an example of the scanner holder 114 in FIG. 1. Also illustrated in FIG. 4 is a robotic arm 404, which is an example of the robotic manipulator 112 in FIG. 1. The robotic arm 404 is just one example of the robotic manipulator 112. Other examples include a multi-axis machine with a spindle and rotary table, akin to a computer-numerical-control (CNC) mill, a gantry, combinations thereof, and the like. The robotic arm 404 is configured to retrieve a scanner 406 from the scanner holder 402 based on instructions corresponding to a user input or one or more parameters associated with, for example, data of a patient (e.g., patient profile, parameters of the patient's previous examination(s), etc.).

In the illustrated example, the scanner holder 402 is in the shape of a tray and includes multiple rows (e.g., three rows) for holding scanners 406. The scanners 406 are examples of the scanners 116 in FIG. 1. In embodiments, the different positions (e.g., rows) of the scanner holder 402 can hold different types of scanners 406. For instance, a first row 408-1 can hold musculoskeletal (MSK) scanners, a second row 408-2 can hold high-frequency scanners (e.g., that operate above 20 megahertz (MHz)), and a third row 408-3 can hold cardiac scanners. The scanner holder 402 can include any suitable number of rows and/or columns and can hold or secure the scanners 406 in any suitable arrangement. Although the scanners 406 are illustrated as resting in an upright orientation relative to the scanner holder 402 (e.g., with a longitudinal axis 410 of the scanner 406 being orthogonal to the top surface of the scanner holder 402, and with the rear end of the scanner 406 coupled with the scanner holder 402), the scanner 406 can be coupled to the scanner holder 402 in any suitable way. For example, the scanners 406 can be positioned in a prostrate position relative to the top surface of the scanner holder 402 (e.g., placed with the longitudinal axis 410 of the scanner 406 parallel to the top surface of the scanner holder 402).

Figure 5:
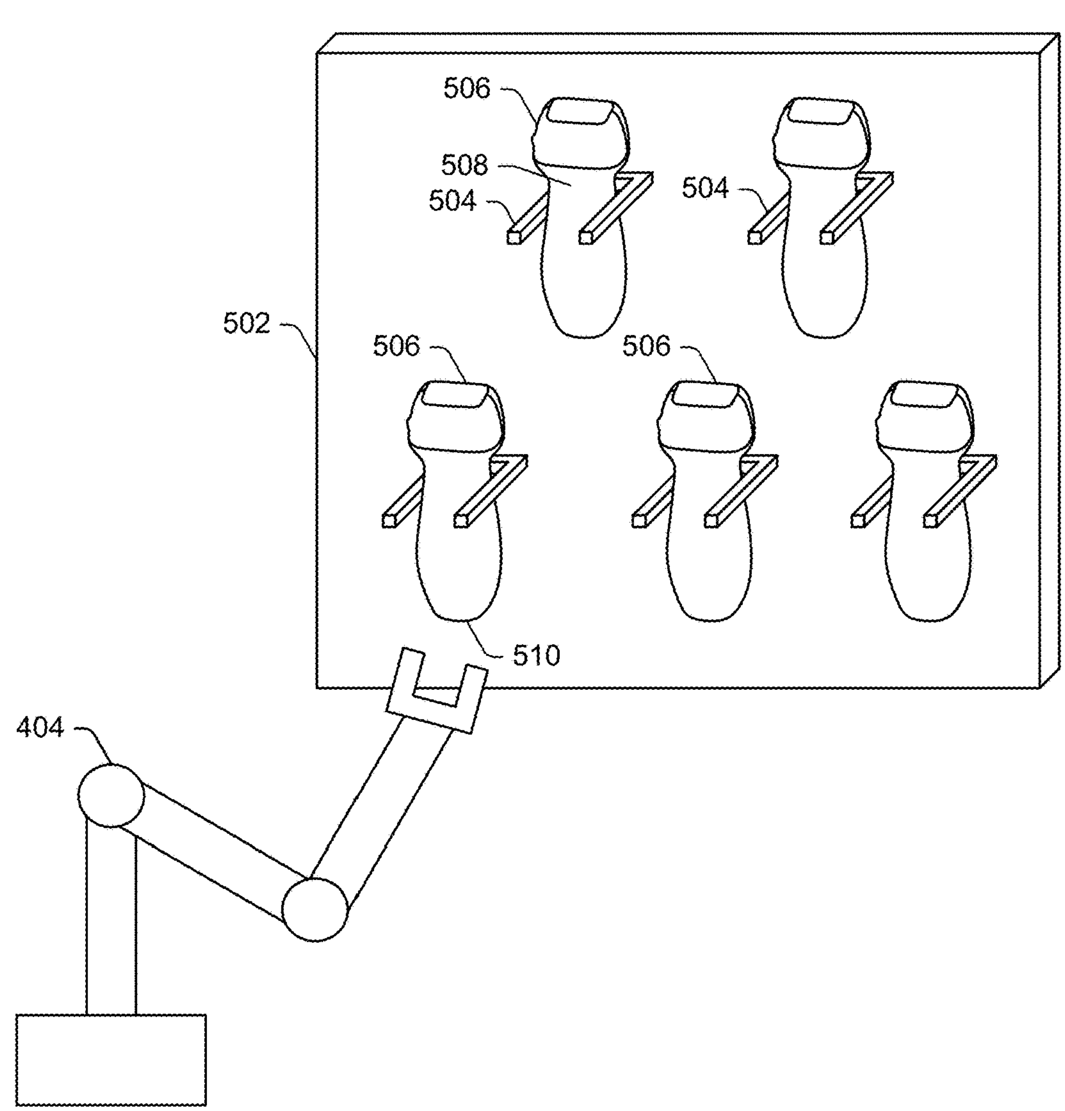
FIG. 5 illustrates an example implementation of another scanner holder, which is part of the ultrasound system from FIG. 1.

FIG. 5 illustrates an example implementation 500 of another scanner holder 502, which is part of the ultrasound system 100 from FIG. 1. The scanner holder 502 is an example of the scanner holder 114 in FIG. 1. In this example, the scanner holder 502 includes a plurality of couplers 504 (e.g., hooks, pegs, cantilevers, etc.) that secure or hold scanners 506 (e.g., scanners 116), using a biasing force against the scanner 506 or holding the scanners 506 at a narrow section (e.g., neck 508) to support the scanner 506 against gravity. The couplers 504 can be mounted to a surface, such as a wall or other substantially vertical object. In some examples, the couplers 504 can be attached to an overhanging surface. These examples can enable the robotic arm 404 to couple to the rear end (e.g., end 510) of the scanner 506, which is the end opposite the transducer of the scanner 506. By coupling to the rear end of the scanner 506, the robotic arm 404 can hold the scanner 506 such that the transducer is directed away from the robotic arm 404 and toward the patient.

Figure 6:
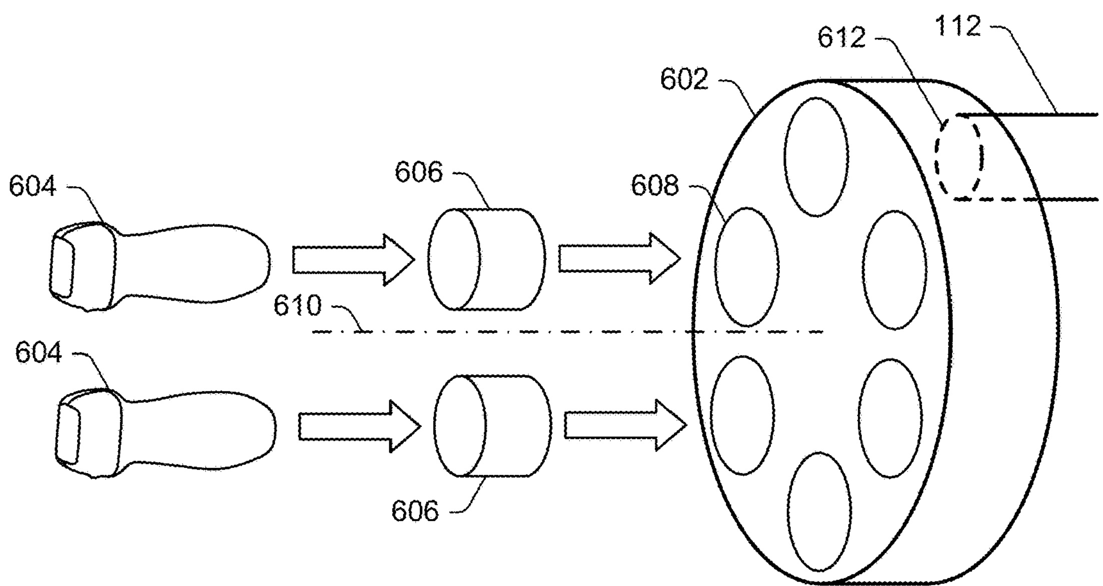
FIG. 6 illustrates an example implementation of another scanner holder, which is part of the ultrasound system from FIG. 1.

FIG. 6 illustrates an example implementation 600 of another scanner holder 602, which is part of the ultrasound system 100 from FIG. 1. The scanner holder 602 is an example of the scanner holder 114 in FIG. 1. The scanner holder 602 can be an automatic tool changer (ATC). For example, the scanner holder 602 is a tool magazine in the shape of a disc, which can hold multiple scanners 604. The scanner 604 can be inserted into a protective holder 606, and the protective holder 606 can be inserted into a slot 608 of the scanner holder 602 (or the scanner holder 402). In embodiments, the scanners 604 and the robotic manipulator 112 are implemented with an ATC protocol that defines how the scanners 604 are maintained by the scanner holders 402 and 602 and used by the robotic manipulator 112 for scanning.

The scanner holder 602 can be integrated with the robotic manipulator 112. In one example, the scanner holder 602 is coupled to a distal end of the robotic manipulator 112 (e.g., "neck" of robotic manipulator 112, which is opposite a base end coupled to the ultrasound system 100) for selecting a scanner and operating the selected scanner for scanning. For example, the robotic manipulator 112 can rotate the scanner holder 602 about a central axis 610 of the scanner holder 602 to switch between scanners 604 in the scanner holder 602 and align one of the scanners 604 with a particular position usable to couple the scanner 604 to circuitry (e.g., circuitry 612) of the robotic manipulator 112 for providing power to the scanner 604 and for operating the scanner 604. The other scanners 604 that are secured in the scanner holder 602 can remain in their respective slots 608. In some aspects, instead of or in addition to holding multiple scanners 604, the scanner holder 602 can hold multiple transducer arrays or scan heads in the protective holders 606 and/or the slots 608. The multiple transducer arrays or scan heads can be interchangeable with a body of one of the scanners 604, and the robotic manipulator 112 can rotate the scanner holder 602 about the central axis 610 to switch between the transducer arrays or scan heads and align one of the transducer arrays or scan heads with the body of the scanner 604 for operation.

Figure 7:
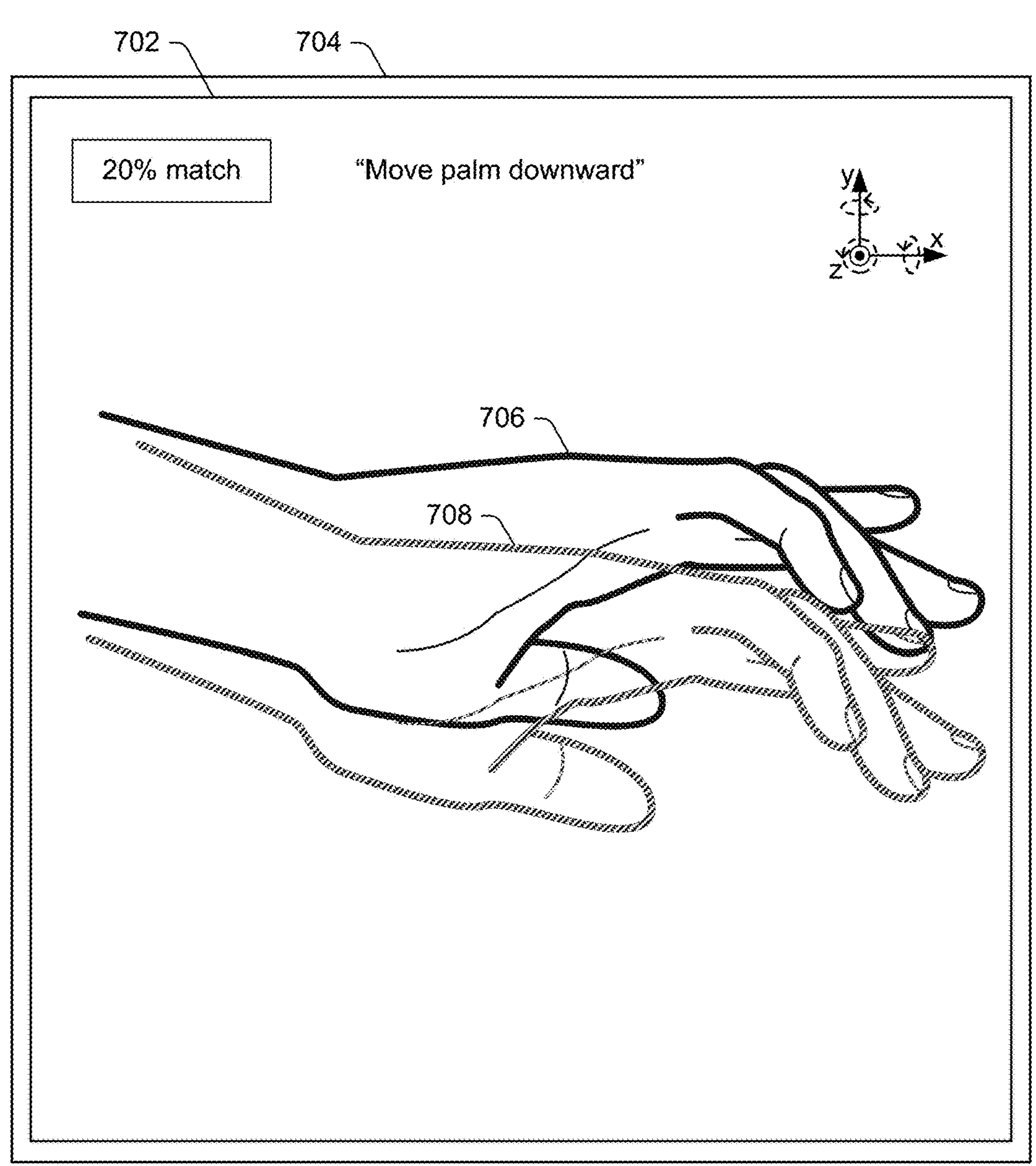
FIG. 7 illustrates an example implementation of a user interface, which is part of the ultrasound system 100 of FIG. 1.

FIG. 7 illustrates an example implementation 700 of a user interface 702 (e.g., graphical user interface), which is part of the ultrasound system 100 of FIG. 1. The user interface 702 can be displayed via a display device 704 associated with and/or communicably coupled to the ultrasound system 100. In aspects, the ultrasound system 100 includes the display device 704. For instance, the display device can be included as part of ultrasound system or the ultrasound scanner 116.

The ultrasound system 100 can display a previously captured image (e.g., 3D rendering, a 3D computer model, a 3D image) of the patient anatomy as an overlay via the user interface 702. Under the overlay, the ultrasound system 100 can display a real-time image of the patient anatomy. Such display can enable the patient to move their anatomy to try to match the previously captured image, which represents the position of the patient anatomy in the previous ultrasound examination. Alternatively, the previously captured image can be displayed as a background layer and the real-time image can be rendered over (in front of) the previously captured image.

In an example, the patient can place their hand within the vessel 202 and the actuators and/or sensors 210 coupled or affixed to the vessel 202 can detect the position and orientation of the hand relative to the vessel 202. The detected position and orientation of the hand is used to generate a real-time image 706 of the hand via the user interface 702. The ultrasound system 100 also displays a previous image 708 or model of the patient's hand captured during a previous ultrasound examination and stored in the database 130, where the previous image 708 is overlaid over (or layered under) the real-time image 706. In one example, the previous image 708 is displayed as a faded or semi-transparent image. The patient can then adjust the position of their hand to try to match the stored image 706.

In some implementations, the ultrasound system 100 can calculate a degree of matching between the 3D position and orientation of the hand in the previous image 708 versus the 3D position and orientation of the hand in the real-time image 706. In aspects, the degree of matching is determined by a neural network (e.g., machine-learning model). The degree of matching can be compared to a threshold value, which indicates whether the position and orientation of the hand in the real-time image 706 is acceptable to perform the ultrasound examination. In addition, instructions can be provided to the patient to guide the patient in moving their anatomy toward matching the position and orientation of the anatomy in the previous image 708 (e.g., "Move palm downward," "Twist wrist clockwise," "Straighten index finger," etc.). In an example, the user interface 702 can display written instructions and/or one or more speakers of the ultrasound system 100 can output audio instructions. A visual and/or audible indication can be provided as the degree of matching crosses the threshold. For example, the user interface 702 can change colors or brightness, the previous image 708 can change colors or disappear, etc.

In some implementations, the position of the patient anatomy relative to the vessel can differ from the previous position used in the previous examination by a degree of rotation about an axis (e.g., the x-axis). Some rotation of the patient anatomy can be accounted for in the movement instructions generated and provided to the robotic manipulator 112 to facilitate a repeatable ultrasound. For example, the movement instructions can cause the robotic manipulator 112 to adjust the orientation (e.g., rotation about an axis) or position (e.g., translational movement along an axis) of the ultrasound scanner 116-1 relative to the current position of the patient anatomy to perform the ultrasound scan of the patient anatomy according to the ultrasound protocols (e.g., angle, depth, gain, etc.) used in the previous examination. Such movement instructions enable the patient anatomy to be scanned in substantially the same manner as the previous examination, resulting in ultrasound data and images that can be compared to one another for diagnostic and procedural purposes, such as identifying inflammation, erosion, or other changes to the patient anatomy.

In an example, the real-time image 706 and the previous image 708 can be displayed in combination with the anatomy fixture 124. In some cases, the anatomy fixture 124 is the 3D digital model of the patient anatomy.

Other information can also be presented via the user interface 702. For example, the information can include steps on how to generate the fixture, steps being performed to generate the fixture, a completion status of the anatomy fixture, etc. A 3D rendering of the patient anatomy can be presented via the user interface 702. In some implementations, the operator may provide input to rotate the 3D rendering about an axis or move the 3D rendering along an axis. The user input can also slice the 3D rendering along a plane or datum to view the 3D rendering of the patient anatomy along the slice.

Example Methods

FIGS. 8-11 depict methods 800, 900, 1000, and 1100, respectively for repeatable ultrasound. The methods 800, 900, 1000, and 1100 are shown as a set of blocks that specify operations performed but are not necessarily limited to the order or combinations shown for performing the operations by the respective blocks. Further, any of one or more of the operations can be repeated, combined, reorganized, or linked to provide a wide array of additional and/or alternate methods. In portions of the following discussion, reference can be made to the example system 100 of FIG. 1 or to entities or processes as detailed in FIGS. 2-7, reference to which is made for example only. The techniques are not limited to performance by one entity or multiple entities operating on one device.

Figure 8:
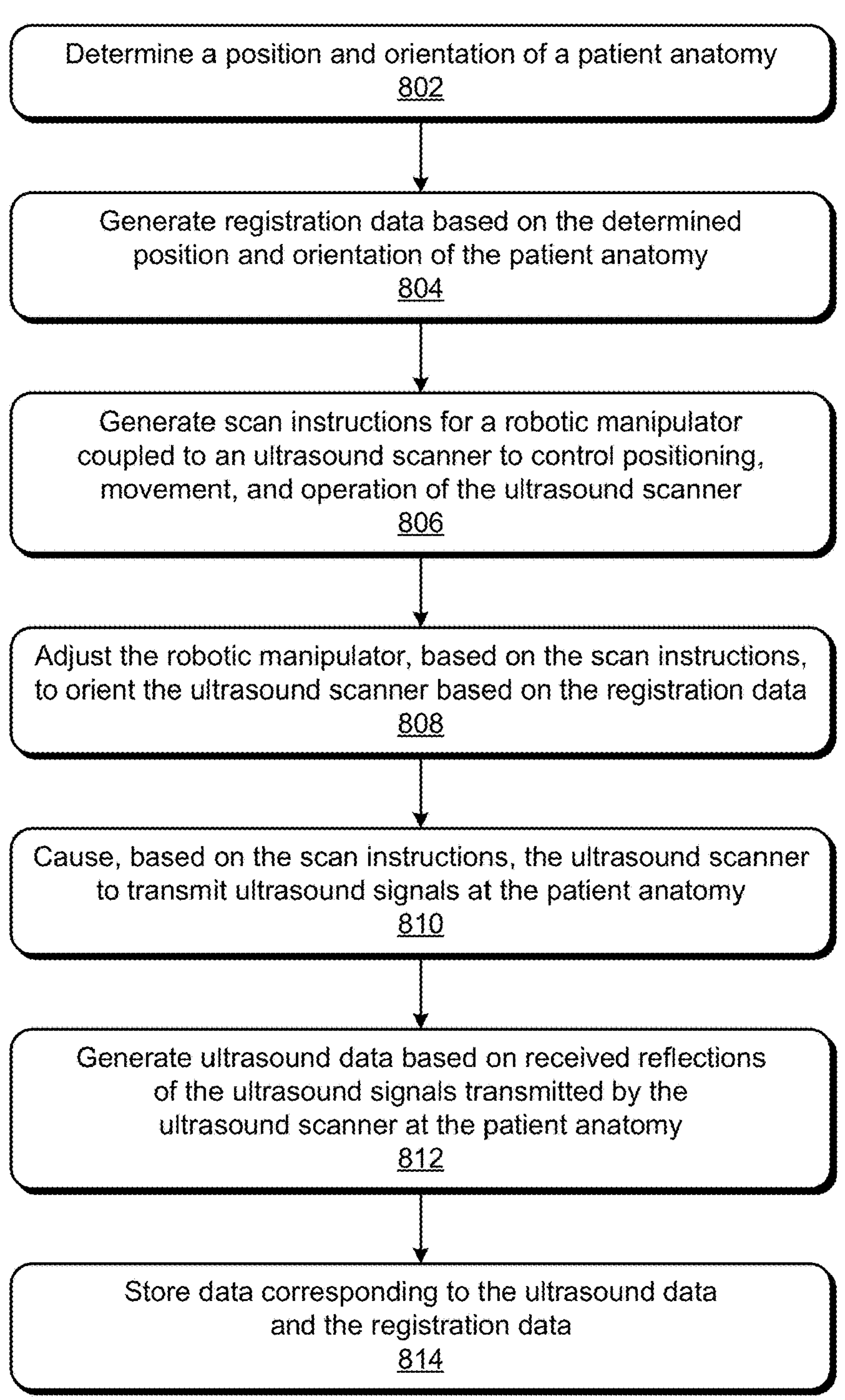
FIG. 8 depicts a method for repeatable ultrasound, in accordance with one or more implementations.

FIG. 8 depicts a method 800 for repeatable ultrasound, in accordance with one or more implementations. The method 800 can be performed by the ultrasound system 100. At 802, a position and orientation of a patient anatomy are determined. For example, the adaptive-registration system 200 can use the one or more sensors 210 to detect the position and orientation of the patient anatomy relative to the sensors 210, the vessel 202, the anatomy fixture 124, or the scanner 116.

At 804, registration data is generated based on the determined position and orientation of the patient anatomy. For example, the fixture generator 104 can generate the anatomy-registration data 126 corresponding to a detected position and orientation of the patient anatomy 120 in the vessel 102. Further, the fixture generator 104 can provide the anatomy-registration data 126 to the position controller 108 to direct movement and operation of the robotic manipulator 112.

At 806, scan instructions are generated for a robotic manipulator coupled to an ultrasound scanner to control positioning, movement, and operation of the ultrasound scanner. For example, the processor system 110 generates the scan instructions 142 for the robotic manipulator 112 to control positioning, movement, and operation of the ultrasound scanner 116-1. The scan instructions can include instructions to select and retrieve a scanner from a plurality of scanners from a scanner holder based on the patient anatomy and move the selected scanner according to the movement instructions from an adaptive-registration system.

At 808, the robotic manipulator is adjusted, based on the scan instructions, to orient the ultrasound scanner based on the determined position and orientation of the patient anatomy. For example, the scan instructions 142 can include the movement instructions 136 for moving, or adjusting a position of, the robotic manipulator 112 in order to move the ultrasound scanner 116-1. The movement instructions 136 can be based on the anatomy-registration data 126 and configured to direct the robotic manipulator to move in a manner that enables the ultrasound scanner 116-1 to generate ultrasound data. The scanner-configuration data 140 can also be generated to indicate position data of the ultrasound scanner relative to the patient anatomy or a coordinate system (3D coordinate system, 4D coordinate system, etc.).

At 810, the ultrasound scanner is caused, based on the scan instructions, to transmit ultrasound signals at the patient anatomy. For example, the scan instructions 142 can cause the robotic manipulator 112 to initiate the ultrasound scanner 116-1 to transmit the ultrasound signals 122 at the patient anatomy 120.

At 812, ultrasound data is generated based on received reflections of the ultrasound signals transmitted by the ultrasound scanner at the patient anatomy. For example, processor system 110 receives the scan data 138 from the ultrasound scanner 116. The processor system 110 can then generate ultrasound data corresponding to the scan data 138.

At 814, data corresponding to the ultrasound data and the registration data is stored. For example, the database 130 can store data associated with the ultrasound data and the anatomy-registration data 126. The stored data can include images, the scan data 138, the ultrasound data, the anatomy-registration data 126, the scanner-configuration data 140, the registration data 128, etc. In aspects, the registration data is image-based, sensor-based, or both.

Figure 9:
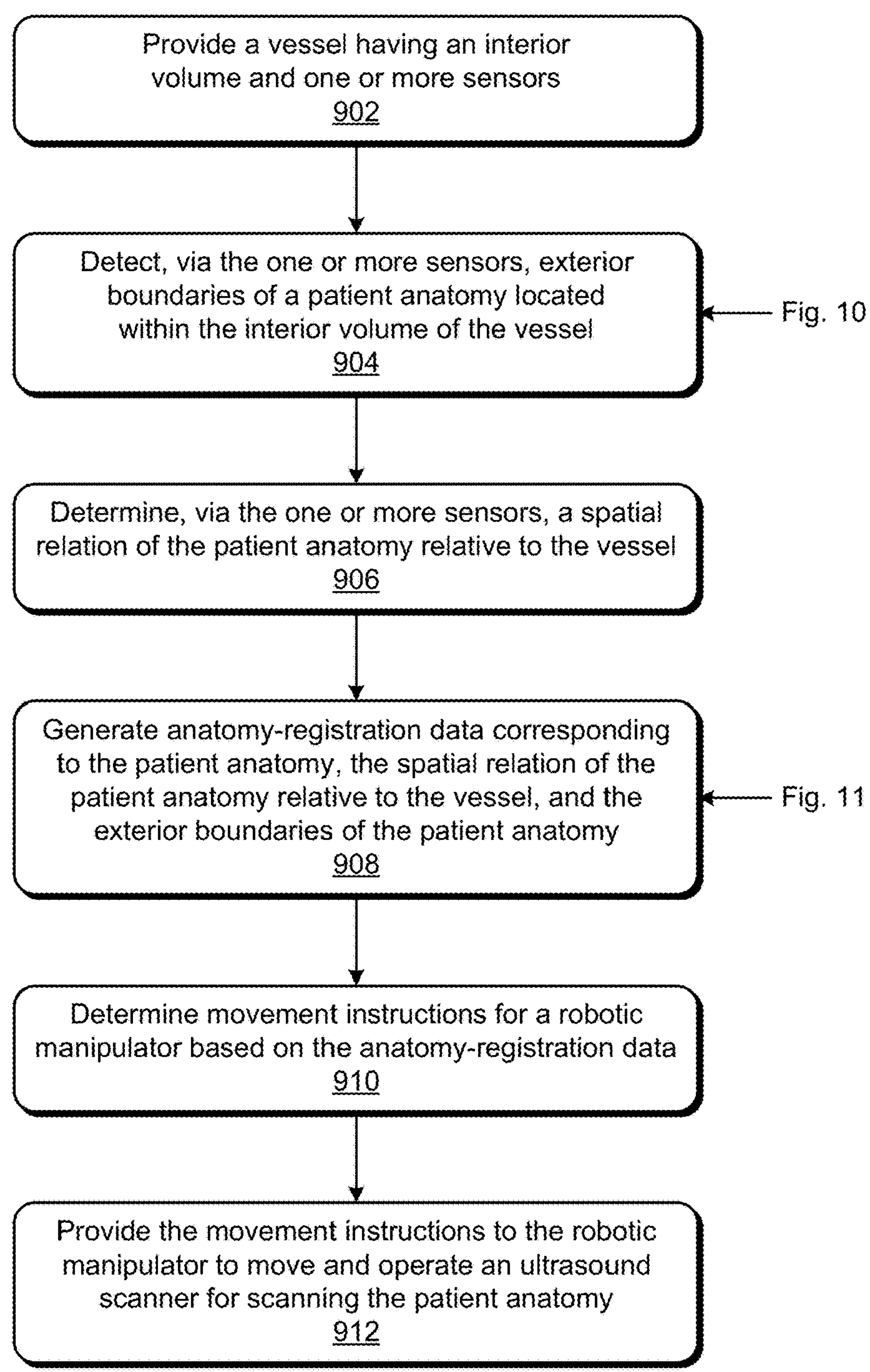
FIG. 9 depicts a method for repeatable ultrasound, in accordance with one or more implementations.

FIG. 9 depicts a method 900 for repeatable ultrasound, in accordance with one or more implementations. The method 900 can be performed by the ultrasound system 100. At 902, a vessel having an interior volume and one or more sensors is provided. The vessel can be vessel 102 and can be any suitable container in which the patient can place their anatomy. In some aspects, the vessel holds or contains the coupling agent 118 in the interior volume.

At 904, exterior boundaries of a patient anatomy located within the interior volume of the vessel are detected via one or more sensors. For example, the sensors 210 can detect the location of the outer edges of the patient anatomy relative to the vessel 202.

At 906, a spatial relation of the patient anatomy relative to the vessel is determined via the one or more sensors. In addition to detecting the exterior boundaries of the patient anatomy, the sensors also determine the spatial relation of the patient anatomy relative to the vessel. The spatial relation includes the 3D position and orientation of the patient anatomy relative to the vessel.

At 908, anatomy-registration data corresponding to the patient anatomy, the spatial relation of the patient anatomy relative to the vessel, and the exterior boundaries of the patient anatomy is determined. The ultrasound system 100 determines, for example, the anatomy-registration data 126 based on the sensor information related to the patient anatomy 120.

At 910, movement instructions are determined for a robotic manipulator based on the anatomy-registration data. For example, the ultrasound system 100 determines movement instructions for moving and operating the robotic manipulator 112 in a manner that avoids colliding with the patient anatomy 120.

At 912, the movement instructions are provided to the robotic manipulator to move and operate an ultrasound scanner for scanning the patient anatomy. For example, the ultrasound system 100 provides the movement instructions 136 to the robotic manipulator 112 to cause the robotic manipulator 112 to move and operate the ultrasound scanner 116 for scanning the patient anatomy 120.

Figure 10:
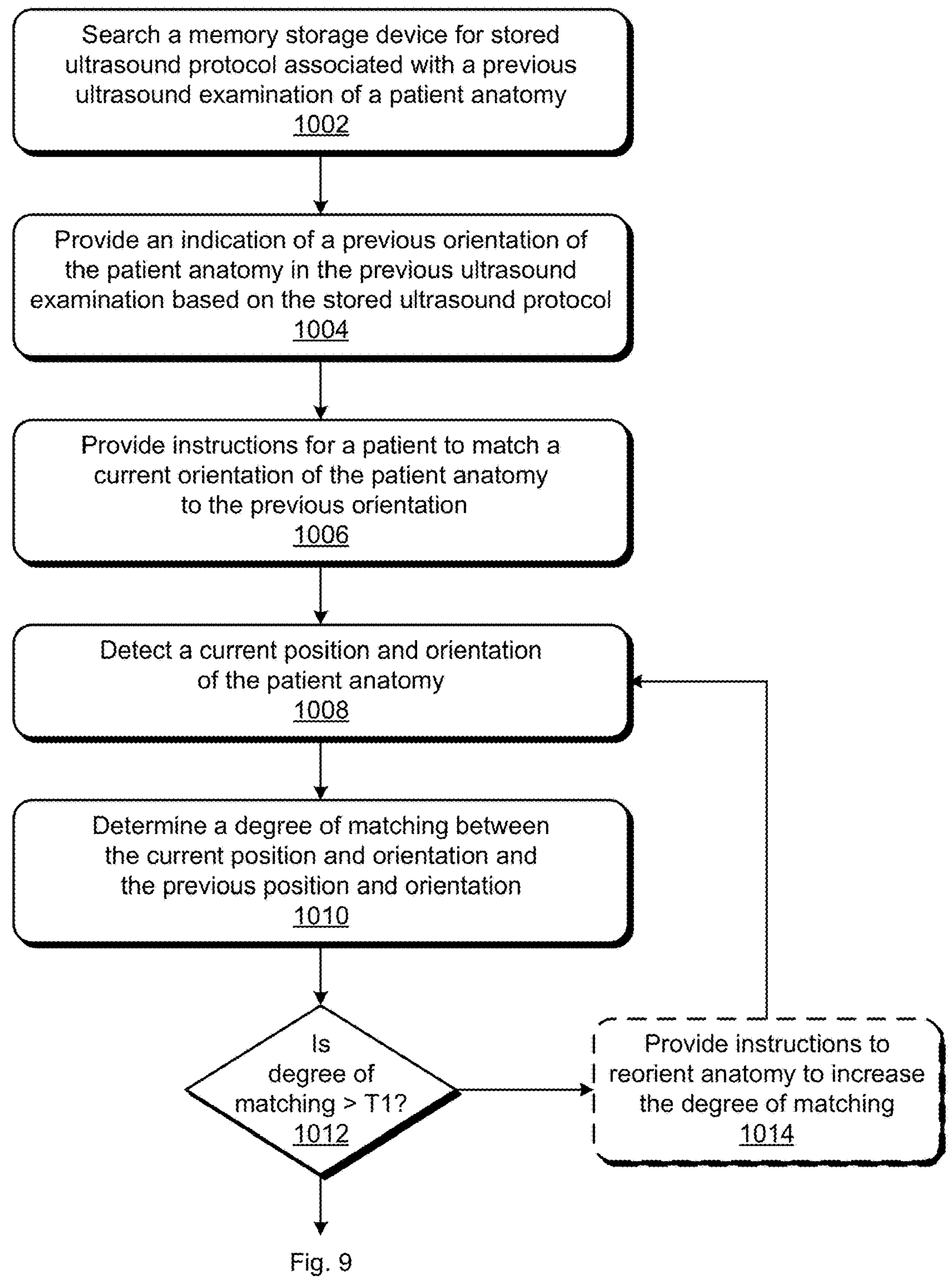
FIG. 10 depicts a method for repeatable ultrasound, in accordance with one or more implementations.

FIG. 10 depicts a method 1000 for repeatable ultrasound, in accordance with one or more implementations. The method 1000 can be performed by the ultrasound system 100. At 1002, a memory storage device is searched for stored ultrasound protocol associated with a previous ultrasound examination of a patient anatomy (e.g., associated with settings and operation of the ultrasound system, including the scanner-configuration data 140, during the ultrasound examination). For example, the database 130 can be searched to access and retrieve registration data 128 and scan instructions 142 that were used during a previous ultrasound examination of the patient anatomy 120. This same ultrasound protocol can be used to repeat the ultrasound examination to provide new ultrasound data that is comparable to previous ultrasound data generated during the previous examination.

At 1004, an indication of a previous position and orientation of the patient anatomy in the previous ultrasound examination is provided based on the stored ultrasound protocol. For example, a 3D rendering of the patient anatomy in the previous orientation can be displayed via the user interface 702 of the display device 704. The user interface 702 can provide a visual reference of the positioning of the patient anatomy for the patient to try to mimic in the present ultrasound examination. In another example, the anatomy-capture device 302 includes actuators that move and position the array of pins 304 to generate a negative (e.g., impression or imprint) of at least a portion of the patient anatomy, where the negative corresponds to the previous position and orientation of the patient anatomy.

At 1006, instructions are provided to a patient to orient the patient anatomy to match the previous orientation. For example, instructions can be displayed via the user interface 702 and/or output via an audio output device (e.g., speaker) to guide the patient to match the current position and/or orientation of their anatomy to the previous position and orientation used in the previous ultrasound examination.

At 1008, a current position and orientation of the patient anatomy is detected. For example, the adaptive-registration system 200 (e.g., using the one or more sensors 210) can detect the current position and orientation of the patient anatomy in the vessel 202. In some aspects, the adaptive-registration system 200 can include one or more patient-worn components (e.g., 204, 206, 208) having one or more sensors or actuators that are in communication with the one or more sensors 210 coupled to the vessel 202. Further, the adaptive-registration system 200 can be configured to generate the registration data with a spatial relation of the patient anatomy 120 with respect to the vessel 202 based on positions of the patient-worn components as detected by the one or more sensors 210 coupled to the vessel.

At 1010, a degree of matching between the current orientation and the previous orientation is determined. For example, the ultrasound system 100 can quantify how closely the current position and orientation of the patient anatomy in the real-time image 706 matches the previous position and orientation of the patient anatomy in the previous image 708. In some aspects, a neural network is used to determine the degree of matching between the determined position and orientation of the patient anatomy and the previous position and orientation of the patient anatomy from the previous ultrasound examination.

At 1012, the ultrasound system determines if the degree of matching exceeds a threshold matching value. If the current position and orientation substantially matches the previous position and orientation (e.g., by 90% or more), then the current position and orientation can be suitable for repeatable ultrasound. If the current position and orientation are too different from the previous position and orientation, then the ultrasound data generated from the current ultrasound examination can be difficult to compare with the previous ultrasound data for purposes of identifying or diagnosing advances in a medical condition such as rheumatoid arthritis.

If the degree of matching does not exceed the threshold matching value (e.g., "NO" at 1012), then optionally at 1014, instructions are provided to the patient to adjust (e.g., reorient) the current position and orientation of the patient anatomy to increase the degree of matching between the current position and orientation and the previous position and orientation. The instructions can be visible instructions displayed via the user interface 702 and/or audio instructions output via a speaker.

Then, the method 1000 returns to 1008 to detect a new (e.g., adjusted) current position and orientation of the patient anatomy. For example, after the patient moves their anatomy, the method 1000 detects the new current position and orientation of the patient anatomy and recalculates the degree of matching according to the new current position and orientation. These steps can be performed in real time as the patient continues to move their anatomy to try to match the previous position and orientation.

If at 1012, the degree of matching exceeds the threshold matching value (e.g., "YES" at 1012), then the method 1000 proceeds to FIG. 9 (e.g., at 904) to utilize a robotic manipulator to perform an ultrasound scan of the patient anatomy in the current position and orientation. For example, when the patient succeeds in substantially matching the current (or new current) position and orientation to the previous position and orientation (e.g., by a 90% or more match), the ultrasound system 100 can initiate the ultrasound examination by determining movement instructions 136 for the robotic manipulator 112 to use for holding and operating the ultrasound scanner 116 in a way to repeat the previous ultrasound examination (e.g., by scanning the patient anatomy according to the same ultrasound protocol used in the previous ultrasound examination).

Figure 11:
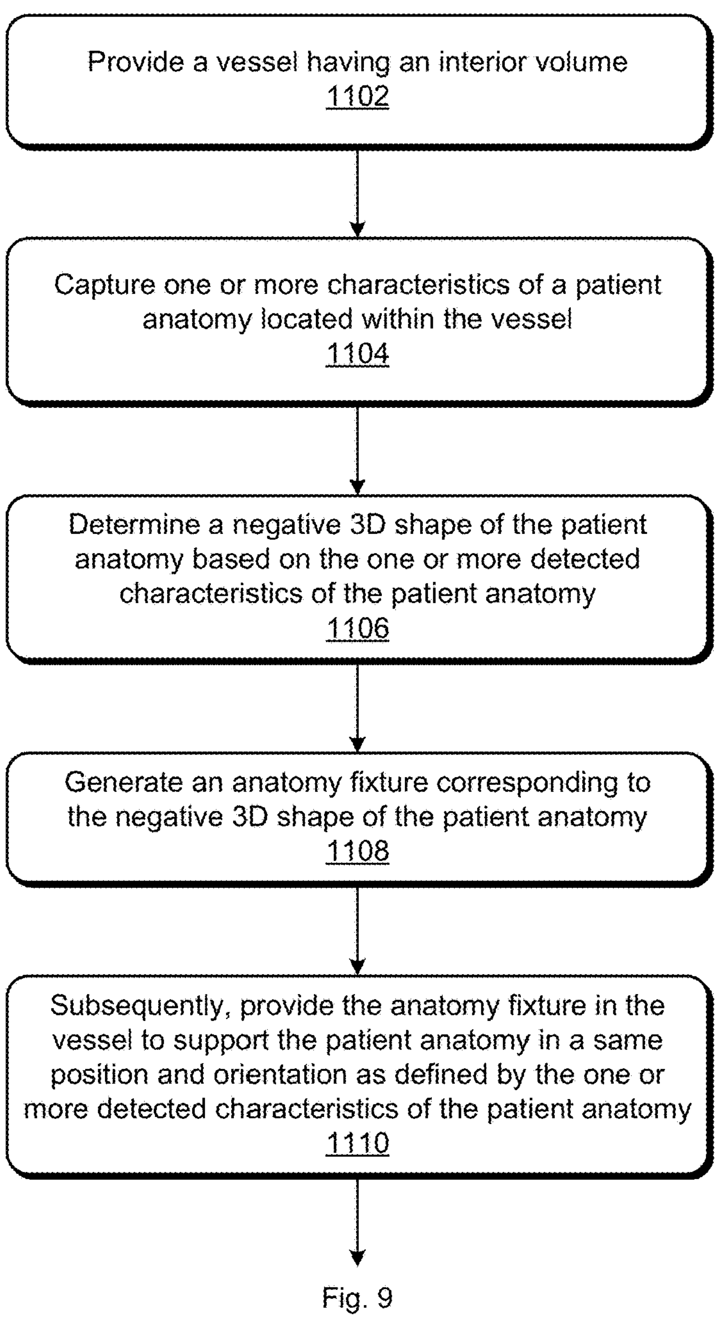
FIG. 11 depicts a method for generating an anatomy fixture for repeatable ultrasound, in accordance with one or more implementations.

FIG. 11 depicts a method 1100 for generating an anatomy fixture for repeatable ultrasound, in accordance with one or more implementations. The method 1100 can be performed by the ultrasound system 100. At 1102, a vessel having an interior volume is provided. The vessel can be vessel 102 and can be any suitable container in which the patient can place their anatomy. In some aspects, the vessel 102 holds or contains the coupling agent 118 in the interior volume. In an example, the vessel is provided during a first ultrasound examination of the patient anatomy 120. The coupling agent 118 can conform to the patient anatomy 120 and act as a conductor that facilitates transmission of the ultrasound signals 122 between the ultrasound scanner 116-1 and the patient anatomy 120.

At 1104, one or more characteristics of a patient anatomy located within the vessel are detected. For example, the anatomy-capture device 106 can capture or detect characteristics such as shape, position, orientation, and/or exterior boundaries (e.g., contour) of the patient anatomy, as disclosed herein. In aspects, the one or more characteristics are captured by the anatomy fixture 124, which can be formed from a shape-adapting material, a shape-adapting mechanism (e.g., anatomy-capture device 302 with the array of pins 304), or a three-dimensional computer model. The one or more characteristic can be captured by the adaptive-registration system 200 having the one or more sensors 210 coupled to the vessel 202, which are configured to detect the position and orientation of the patient anatomy 120 located within the vessel 202 and generate corresponding sensor data.

At 1106, a negative 3D shape of the patient anatomy is determined based on the one or more detected characteristics. The characteristics can be used to determine, for example, data usable to create a mold configured to support the patient anatomy. The negative 3D shape of the patient anatomy can be determined using, for example, the array of pins 304, where each pin in the array of pins 304 has a central axis and is displaceable along the central axis, and a plurality of sensors configured to detect a depth and location of each pin of the array of pins 304 as the patient anatomy 120 displaces a subset of the pins 304. The depth and location of each pins can be recorded as the registration data to represent a negative of a contour of an exterior surface of a portion of the patient anatomy 120. In some implementations, the anatomy fixture 124 includes a plurality of actuators, where one or more of the actuators is configured to, at a subsequent time, displace at least some of the pins 304 of the array of pins 304 based on the registration data to generate the negative of the contour of the exterior surface of the portion of the patient anatomy 120. In some aspects, information can be provided via the user interface 702, where the information includes steps on how to generate the anatomy fixture, steps being performed to generate the anatomy fixture, or a completion status of the anatomy fixture.

At 1108, an anatomy fixture is generated based on the negative 3D shape of the patient anatomy. For example, the fixture generator 104 generates the anatomy fixture 124 based on characteristics of the patient anatomy 120 that are captured by the anatomy-capture device 106. The anatomy fixture 124 can include any suitable fixture, such as a mold, 3D computer model, a shape-adapting material, a shape-adapting mechanism, etc. In addition, the anatomy fixture can represent a negative of at least a portion of the patient anatomy 120 and can be used to support the patient anatomy 120 or provide a reference to a particular position and orientation of the patient anatomy 120 as defined in the first ultrasound examination.

The anatomy fixture defines at least a portion of the exterior boundaries (e.g., outline) of the patient anatomy. These defined boundaries combined with the characteristics (e.g., shape, size, etc.) provide an indication of a remaining portion of the exterior boundaries of the patient anatomy that are not defined by the anatomy fixture alone. For example, the array of pins 304 of the anatomy fixture 124 can define the contour of approximately half of a patient's hand (e.g., palm-side of hand facing the anatomy fixture) but the surface of the back of the hand is not defined by the anatomy fixture 124. In this case, the data including the detected shape, size, etc. of the hand can be combined with the anatomy fixture 124 to define the location of the surface of the back of the hand relative to the anatomy fixture itself. Such information can be used, for example, to avoid causing the ultrasound scanner 116 to collide with the back of the patient's hand.

At 1110, at a subsequent time (e.g., during a subsequent ultrasound examination), the anatomy fixture is provided to support the patient anatomy in a same position and orientation as defined by the one or more detected characteristics of the patient anatomy detected in the first ultrasound examination. The anatomy fixture 124 can support the patient anatomy 120 in the same position and orientation across multiple serial ultrasound examinations. The placement of the anatomy fixture in the vessel 102 can define the spatial relation (e.g., position and orientation) of the patient anatomy 120 relative to the vessel 102. The method 1100 can then proceed to FIG. 9 (e.g., at 904) to utilize the robotic manipulator 112 to perform an ultrasound scan of the patient anatomy 120.

Example Models and Devices

As described, many of the features described herein can be implemented using a machine-learned model. For the purposes of this disclosure, a machine-learned model is any model that accepts an input, analyzes, and/or processes the input based on an algorithm derived via machine-learning training, and provides an output. A machine-learned model can be conceptualized as a mathematical function of the following form:

$$f(\hat{s},\theta)=\hat{y} \quad \text{Equation (1)}$$

In Equation (1), the operator f represents the processing of the machine-learned model based on an input and providing an output. The term s represents a model input, such as ultrasound data. The model analyzes/processes the input s using parameters θ to generate output ŷ (e.g., the anatomy-registration data 126, degree of matching between positions and orientations of a patient anatomy in current and previous ultrasound examinations, etc.). Both ŝ and ŷ can be scalar values, matrices, vectors, or mathematical representations of phenomena such as categories, classifications, image characteristics, the images themselves, text, labels, or the like. The parameters θ can be any suitable mathematical operations, including but not limited to applications of weights and biases, filter coefficients, summations or other aggregations of data inputs, distribution parameters such as mean and variance in a Gaussian distribution, linear-algebra-based operators, or other parameters, including combinations of different parameters, suitable to map data to the desired output.

Figure 12:
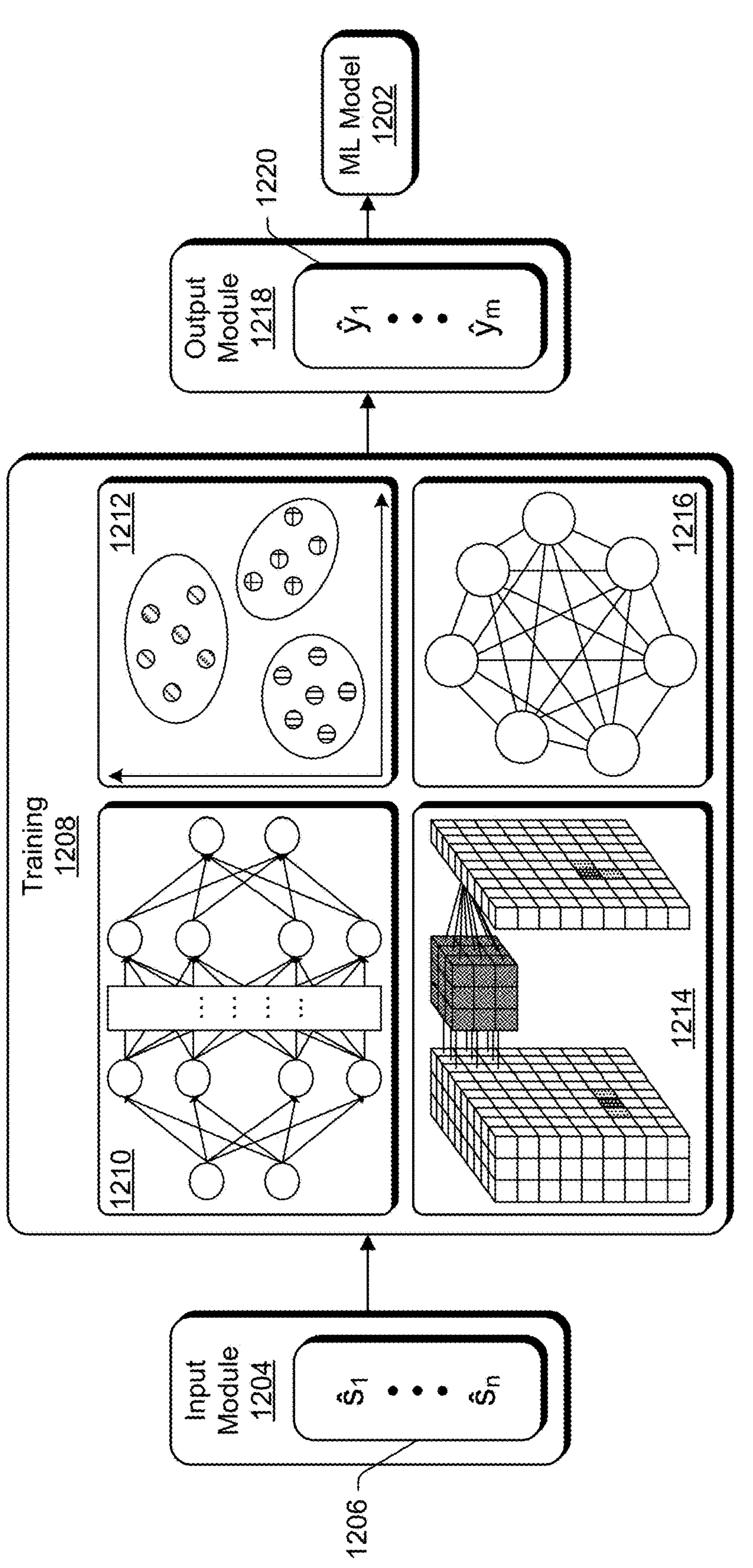
FIG. 12 represents an example machine-learning architecture used to train a machine-learned model M, which can be used to implement at least some of the techniques disclosed herein.

FIG. 12 represents an example machine-learning architecture 1200 used to train a machine-learned model M 1202, which can be used to implement at least some of the techniques disclosed herein. An input module 1204 accepts an input ŝ 1206, which can be an array with members $\hat{s}_1$ through $\hat{s}_n$. The input ŝ 1206 is fed into a training module 1208, which processes the input ŝ 1206 based on the machine-learning architecture 1200. For example, if the machine-learning architecture 1200 uses a multilayer perceptron (MLP) model 1210, the training module 1208 applies weights and biases to the input ŝ 1206 through one or more layers of perceptrons, each perceptron performing a fit using its own weights and biases according to its given functional form. MLP weights and biases can be adjusted so that they are optimized against a least mean square, logcosh, or other optimization function (e.g., loss function) known in the art. Although an MLP model 1210 is described here as an example, any suitable machine-learning technique can be employed, some examples of which include but are not limited to k-means clustering 1212, convolutional neural networks (CNN) 1214, a Boltzmann machine 1216, Gaussian mixture models (GMM), and long short-term memory (LSTM). The training module 1208 provides an input to an output module 1218. The output module 1218 analyzes the input from the training module 1208 and provides a prediction output in the form of ŷ 1220, which can be an array with members $\hat{y}_1$ through $\hat{y}_m$. The prediction output 1220 can represent a known correlation with the input ŝ 1206, such as, for example, anatomy information (e.g., characteristics of the patient anatomy 120).

In some examples, the input ŝ 1206 can be training input labeled with known output correlation values, and these known values can be used to optimize the output ŷ 1220 in training against the optimization/loss function. In other examples, the machine-learning architecture 1200 can categorize the output ŷ 1220 values without being given known correlation values to the inputs ŝ 1206. In some examples, the machine-learning architecture 1200 can be a combination of machine-learning architectures. By way of example, a first network can use input ŝ 1206 and provide prediction output ŷ 1220 as an input $\hat{s}_{ML}$ to a second machine-learned architecture, with the second machine-learning architecture providing a final prediction output $\hat{y}_f$. In another example, one or more machine-learning architectures can be implemented at various points throughout the training module 1208.

In some ML models, all layers of the model are fully connected. For example, all perceptrons in an MLP model act on every member of s. For an MLP model with a 100×100 pixel image as the input, each perceptron provides weights/biases for 10,000 inputs. With a large, densely layered model, this can result in slower processing and/or issues with vanishing and/or exploding gradients. A CNN, which may not be a fully connected model, can process the same image using 5×5 tiled regions, requiring only 25 perceptrons with shared weights, giving much greater efficiency than the fully connected MLP model.

Figure 13:
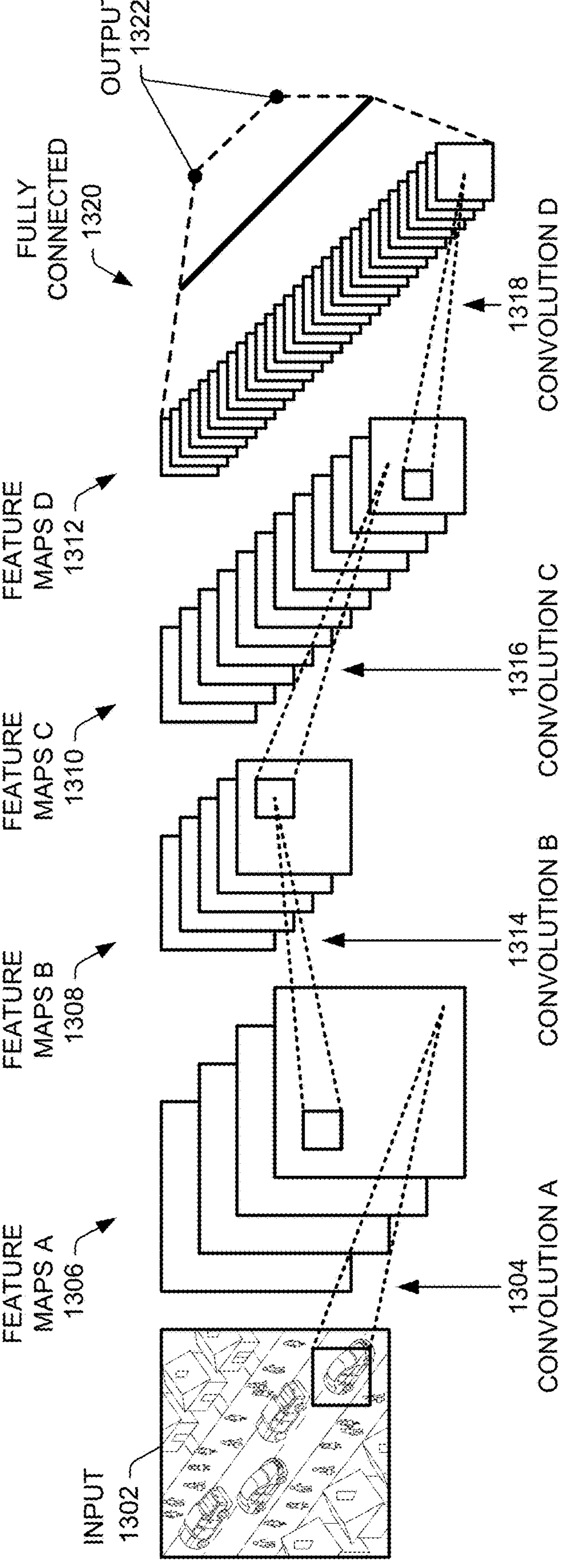
FIG. 13 represents an example model using a Convolutional Neural Network (CNN) to process an input image, which includes representations of objects that can be identified via object recognition.

FIG. 13 represents an example model 1300 using a CNN to process an input image 1302, which includes representations of objects that can be identified via object recognition, such as people or cars. Although this example includes people and cars as general objects in the input image 1302, the input image 1302 can include the ultrasound image 132, as described above, having representations of anatomy, such as bodily structures. Convolution A 1304 can be performed to create a first set of feature maps (e.g., feature maps A 1306). A feature map can be a mapping of aspects of the input image 1302 given by a filter element of the CNN. This process can be repeated using feature maps A 1306 to generate further feature maps B 1308, feature maps C 1310, and feature maps D 1312 using convolution B 1314, convolution C 1316, and convolution D 1318, respectively. In this example, feature maps D 1312 become the input for fully connected network layers 1320. In this way, the ML model can be trained to recognize certain elements of the image, such as people or cars, and provide an output 1322 that, for example, identifies the recognized elements.

Although the example of FIG. 13 shows a CNN as a part of a fully connected network, other architectures are possible and this example should not be seen as limiting. There can be more or fewer layers in the CNN. A CNN component for a model can be placed in a different order, or the model can contain additional components or models. There may be no fully connected components, such as a fully convolutional network. Additional aspects of the CNN, such as pooling, downsampling, upsampling, or other aspects known to people skilled in the art can also be employed.

Figure 14:
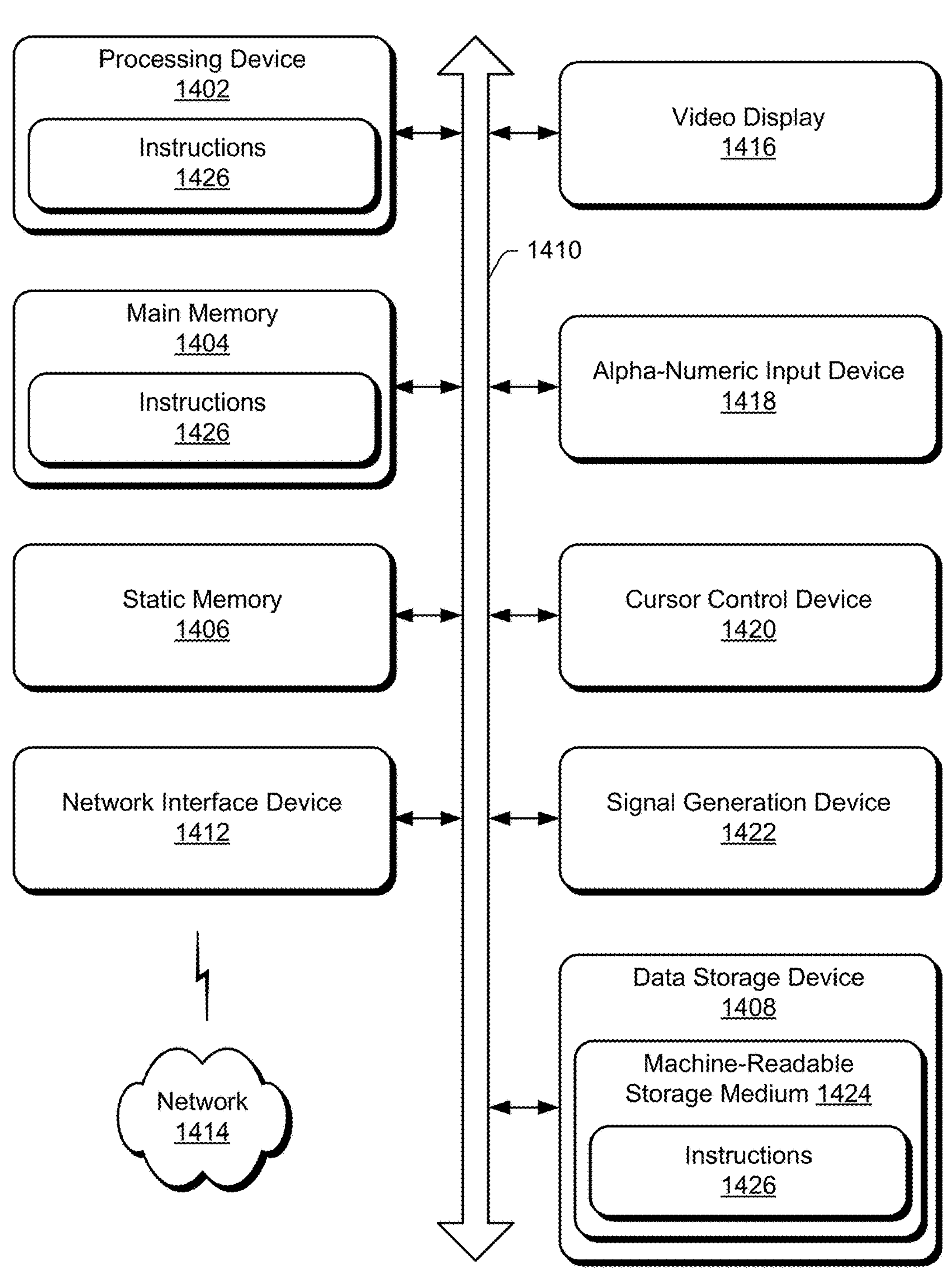
FIG. 14 illustrates a block diagram of an example computing device that can perform one or more of the operations described herein, in accordance with some implementations.

FIG. 14 illustrates a block diagram of an example computing device 1400 that can perform one or more of the operations described herein, in accordance with some implementations. The computing device 1400 can be connected to other computing devices in a local area network (LAN), an intranet, an extranet, and/or the Internet. The computing device can operate in the capacity of a server machine in a client-server network environment or in the capacity of a client in a peer-to-peer network environment. The computing device can be provided by a personal computer (PC), a server computer, a desktop computer, a laptop computer, a tablet computer, a smartphone, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods discussed herein. In some implementations, the computing device 1400 is one or more of an ultrasound machine, an access point, and a packet-forwarding component.

The example computing device 1400 can include a processing device 1402 (a general-purpose processor, a programmable logic device (PLD), etc.), a main memory 1404 (e.g., synchronous dynamic random-access memory (DRAM), read-only memory (ROM)), and a static memory 1406 (e.g., flash memory and a data storage device 1408), which can communicate with each other via a bus 1410. The processing device 1402 can be provided by one or more general-purpose processing devices such as a microprocessor, a central processing unit, or the like. In an illustrative example, the processing device 1402 comprises a complex instruction set computing (CISC) microprocessor, a reduced instruction set computing (RISC) microprocessor, a very long instruction word (VLIW) microprocessor, or a processor implementing other instruction sets or processors implementing a combination of instruction sets. The processing device 1402 can also comprise one or more special-purpose processing devices such as an application-specific integrated circuit (ASIC), a field programmable gate array (FPGA), a digital signal processor (DSP), a network processor, or the like. The processing device 1402 can be configured to execute the operations described herein, in accordance with one or more aspects of the present disclosure, for performing the operations and steps discussed herein.

The computing device 1400 can further include a network interface device 1412, which can communicate with a network 1414. The computing device 1400 also can include a video display unit 1416 (e.g., a liquid crystal display (LCD), organic light-emitting diode (OLED), or a cathode ray tube (CRT)), an alphanumeric input device 1418 (e.g., a keyboard), a cursor control device 1420 (e.g., a mouse), and an acoustic signal generation device 1422 (e.g., a speaker and/or a microphone). In one embodiment, the video display unit 1416, the alphanumeric input device 1418, and the cursor control device 1420 can be combined into a single component or device (e.g., an LCD touch screen).

The data storage device 1408 can include a computer-readable storage medium 1424 on which can be stored one or more sets of instructions 1426 (e.g., instructions for carrying out the operations described herein, in accordance with one or more aspects of the present disclosure). The instructions 1426 can also reside, completely or at least partially, within the main memory 1404 and/or within the processing device 1402 during execution thereof by the computing device 1400, where the main memory 1404 and the processing device 1402 also constitute computer-readable media. The instructions can further be transmitted or received over the network 1414 via the network interface device 1412.

Various techniques are described in the general context of software, hardware elements, or program modules. Generally, such modules include routines, programs, objects, elements, components, data structures, and so forth that perform particular tasks or implement particular abstract data types. The terms "module," "functionality," and "component" as used herein generally represent software, firmware, hardware, or a combination thereof. In some aspects, modules described herein (e.g., the position controller 108, fixture generator 104, etc.) are embodied in the data storage device 1408 of the computing device 1400 as executable instructions or code. Although represented as software implementations, the described modules can be implemented as any form of a control application, software application, signal-processing and control module, hardware, or firmware installed on the computing device 1400.

While the computer-readable storage medium 1424 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding, or carrying a set of instructions for execution by the machine and that causes the machine to perform the methods described herein. The term "computer-readable storage medium" shall accordingly be taken to include, but not be limited to, solid-state memories, optical media, and magnetic media.

CONCLUSION

Embodiments for repeatable ultrasound are disclosed. The repeatable ultrasound techniques disclosed herein provide solutions that enable generation of consistent ultrasound images suitable for the early detection and management of one or more medical conditions, including rheumatoid arthritis. These techniques reduce and/or remove the dependency of the operator and the inconsistencies resulting from patient movement, so that the ultrasound system can generate matching image views needed in serial ultrasound examinations for the assessment and treatment of such medical conditions.

What is claimed is:

1. An ultrasound system comprising:

an ultrasound scanner configured to generate ultrasound data based on received reflections of ultrasound signals transmitted by the ultrasound scanner at a patient anatomy;

a robotic manipulator configured to couple to the ultrasound scanner, the robotic manipulator configured to control positioning, movement, and operation of the ultrasound scanner;

a vessel having an interior volume configured to contain a coupling agent that conforms to the patient anatomy when the patient anatomy is located within the interior volume of the vessel, the coupling agent configured to act as a conductor that facilitates transmission of the ultrasound signals between the ultrasound scanner and the patient anatomy;

a processor system configured to generate scan instructions for the robotic manipulator and receive the ultrasound data from the ultrasound scanner;

an adaptive-registration system configured to determine a position and orientation of the patient anatomy relative to the vessel and adjust the robotic manipulator to orient the ultrasound scanner based on the determined position and orientation of the patient anatomy; and a database configured to store data corresponding to the ultrasound data and anatomy-registration data associated with the determined position and orientation of the patient anatomy.

2. The ultrasound system of claim 1, further comprising a scanner holder configured to hold a plurality of ultrasound scanners, and wherein the robotic manipulator is configured to:

select a scanner from the plurality of ultrasound scanners from the scanner holder based on the patient anatomy;

retrieve the selected scanner from the scanner holder; and move the selected scanner according to movement instructions from the adaptive-registration system, wherein the selected scanner is the ultrasound scanner.

3. The ultrasound system of claim 1, further comprising a position controller configured to generate movement instructions for the robotic manipulator based on the anatomy-registration data, wherein the movement instructions are configured to direct the robotic manipulator to move in a manner that enables the ultrasound scanner to generate the ultrasound data.

4. The ultrasound system of claim 3, wherein the position controller is configured to generate scanner-configuration data for indicating position data of the ultrasound scanner relative to the patient anatomy or a three-dimensional coordinate system.

5. The ultrasound system of claim 1, wherein the anatomy-registration data is image-based registration data.

6. The ultrasound system of claim 1, wherein the anatomy-registration data is sensor-based registration data.

7. The ultrasound system of claim 1, wherein the adaptive-registration system includes:

an anatomy-capture device configured to capture characteristics of the patient anatomy; and a fixture generator configured to generate an anatomy fixture based on the captured characteristics of the patient anatomy, the anatomy fixture configured to support the patient anatomy in the determined position and orientation during an ultrasound examination.

8. The ultrasound system of claim 7, wherein the fixture generator is configured to:

generate the anatomy-registration data; and provide the anatomy-registration data to a position controller configured to direct movement and operation of the robotic manipulator.

9. The ultrasound system of claim 7, wherein the anatomy fixture is formed from a shape-adapting material, a shape-adapting mechanism, or a three-dimensional computer model.

10. The ultrasound system of claim 1, wherein the adaptive-registration system includes one or more sensors coupled to the vessel, wherein the one or more sensors are configured to detect the position and orientation of the patient anatomy located within the vessel and generate corresponding sensor data.

11. The ultrasound system of claim 10, wherein the adaptive-registration system includes a fixture generator configured to:

receive the sensor data from the one or more sensors; and generate an anatomy fixture that is a negative of at least a portion of the patient anatomy and is configured to physically support the patient anatomy in the detected position and orientation during a subsequent ultrasound examination.

12. The ultrasound system of claim 11, further comprising a user interface for providing information including steps on how to generate the anatomy fixture, steps being performed to generate the anatomy fixture, or a completion status of the anatomy fixture.

13. The ultrasound system of claim 10, further comprising one or more patient-worn components having one or more sensors or actuators that are in communication with the one or more sensors coupled to the vessel, wherein the adaptive-registration system is configured to generate the anatomy-registration data with a spatial relation of the patient anatomy with respect to the vessel based on positions of the patient-worn components as detected by the one or more sensors coupled to the vessel.

14. The ultrasound system of claim 1, further comprising a user interface for providing an indication of a previous position and orientation of the patient anatomy from a previous ultrasound examination, wherein:

the database is configured to store ultrasound data including the previous position and orientation of the patient anatomy from the previous ultrasound examination; and the adaptive-registration system is configured to provide an indication of a degree of matching between the determined position and orientation of the patient anatomy and the previous position and orientation of the patient anatomy.

15. The ultrasound system of claim 14, wherein the adaptive-registration system utilizes a neural network to determine the degree of matching between the determined position and orientation of the patient anatomy and the previous position and orientation of the patient anatomy from the previous ultrasound examination.

16. An ultrasound system comprising:

an ultrasound scanner configured to generate ultrasound data based on received reflections of ultrasound signals transmitted by the ultrasound scanner at a patient anatomy;

a robotic manipulator configured to couple to the ultrasound scanner, the robotic manipulator configured to control positioning, movement, and operation of the ultrasound scanner;

a processor system configured to generate scan instructions for the robotic manipulator and receive the ultrasound data from the ultrasound scanner;

an adaptive-registration system configured to determine a position and orientation of the patient anatomy and adjust the robotic manipulator to orient the ultrasound scanner based on the determined position and orientation of the patient anatomy;

a database configured to store data corresponding to the ultrasound data and anatomy-registration data associated with the determined position and orientation of the patient anatomy; and an anatomy fixture including:

an array of pins, each pin in the array of pins having a central axis and being displaceable along the central axis; and a plurality of sensors configured to detect a depth and location of each pin of the array of pins as the patient anatomy displaces a subset of the pins, wherein the depth and location of each pin is recorded as the anatomy-registration data to represent a negative of a contour of an exterior surface of a portion of the patient anatomy.

17. The ultrasound system of claim 16, wherein the anatomy fixture includes a plurality of actuators, wherein one or more actuators of the plurality of actuators is configured to, at a subsequent time, displace at least some of the pins of the array of pins based on the anatomy-registration data to generate the negative of the contour of the exterior surface of the portion of the patient anatomy.

18. A method for repeatable ultrasound, the method comprising:

providing a vessel having an interior volume;

detecting exterior boundaries of a patient anatomy located within the interior volume of the vessel;

detecting a spatial relation of the patient anatomy relative to the vessel;

generating anatomy-registration data corresponding to the patient anatomy based on the spatial relation of the patient anatomy relative to the vessel and the exterior boundaries of the patient anatomy;

determining movement instructions for a robotic manipulator based on the anatomy-registration data; and providing the movement instructions to the robotic manipulator to move and operate an ultrasound scanner for scanning the patient anatomy.

19. The method of claim 18, further comprising:

generating an anatomy fixture based on the exterior boundaries of the patient anatomy and the spatial relation of the patient anatomy relative to the vessel; and providing the anatomy fixture to support the patient anatomy in the same position and orientation across multiple serial ultrasound examinations.

20. The method of claim 18, further comprising:

capturing characteristics of the patient anatomy; and generating an anatomy fixture based on the captured characteristics of the patient anatomy, the anatomy fixture configured to physically support the patient anatomy in the determined position and orientation during an ultrasound examination.

* * * * *